United States Patent
Hagel et al.

(10) Patent No.: US 10,371,695 B2
(45) Date of Patent: Aug. 6, 2019

(54) IDENTIFYING COMPOUNDS MODIFYING A CELLULAR PHENOTYPE

(71) Applicant: 2cureX ApS, Birkerød (DK)

(72) Inventors: Grith Hagel, Dragør (DK); Ole Thastrup, Birkerød (DK)

(73) Assignee: 2cureX ApS, Birkerød (DK)

( * ) Notice: Subject to any disclaimer, the term of this patent is extended or adjusted under 35 U.S.C. 154(b) by 154 days.

(21) Appl. No.: 15/321,888

(22) PCT Filed: Jul. 1, 2015

(86) PCT No.: PCT/DK2015/050197
§ 371 (c)(1),
(2) Date: Dec. 23, 2016

(87) PCT Pub. No.: WO2016/000721
PCT Pub. Date: Jan. 7, 2016

(65) Prior Publication Data
US 2017/0131263 A1    May 11, 2017

(30) Foreign Application Priority Data

Jul. 2, 2014    (DK) .................................. 2014 00357

(51) Int. Cl.
| | | |
|---|---|---|
| *G01N 33/50* | (2006.01) | |
| *C07K 16/28* | (2006.01) | |
| *A61K 31/513* | (2006.01) | |
| *A61K 31/519* | (2006.01) | |
| *A61K 31/555* | (2006.01) | |
| *A61K 31/704* | (2006.01) | |
| *A61K 31/4745* | (2006.01) | |

(52) U.S. Cl.
CPC ...... *G01N 33/5011* (2013.01); *A61K 31/4745* (2013.01); *A61K 31/513* (2013.01); *A61K 31/519* (2013.01); *A61K 31/555* (2013.01); *A61K 31/704* (2013.01); *C07K 16/2863* (2013.01); *G01N 33/5008* (2013.01)

(58) Field of Classification Search
CPC .................................................. G01N 33/5011
USPC ............................................ 506/10; 306/10
See application file for complete search history.

(56) References Cited

U.S. PATENT DOCUMENTS

| | | | | |
|---|---|---|---|---|
| 4,089,748 A | * | 5/1978 | Smernoff | ................. C12N 1/00 435/243 |
| 2010/0252118 A1 | * | 10/2010 | Fraden | ............. B01L 3/502746 137/2 |

FOREIGN PATENT DOCUMENTS

| | | |
|---|---|---|
| WO | WO-2005/116643 | 12/2005 |
| WO | WO-2005/116656 | 12/2005 |

OTHER PUBLICATIONS

T.A. D'Amato et al.,"Survival Among Patients with Platinum Resistant, Locally Advanced Non-Small Cell Lung Cancer Treated with Platinum-Based Systemic Therapy", Ann Surg Oncol, 16: 2848-2855, 2009.
(Anonymous) "Instruction for Mebiol Gel", Cosmo Bio Co. Ltd., Jan. 4, 2003, p. 2pp, retrieved from internet on Oct. 20, 2015, www.comobio.co.jp/export_e/products/cell_tissue_culture/pdf/instruction_manual_CB_20130412.pdf.
(Anonymous) "Mebiol Gel Thermoreversible Hydrogel for 3D Cell Culture and other Applications", Cosmo Bio, Jan. 4, 2003, p. 2pp, retrieved from the Internet on Oct. 20, 2015, www.comobio.co.jp/export_e/catalog/pdf/10115_MBG_Mebiol(R)Gel.pdf.
E. Mechetner, "In vitro drug responses in primary and metastatic colorectal cancers", Scan. Journ. of Gastroenterology, 46, p. 70-78, 2011.
Sato, T., Long-term Expansion of Epithelial Organoids from Human Colon, Adenoma, Adenocarcinoma, and Barrett's Epithelium, Gastroenterology 2011; 141: 1762-1772.
Tardiff et al, "Phenotypic screens for compounds that target the cellular pathologies underlying Parkinson's disease", Drug Discovery Today: Technologies, vol. 10, No. 1, Mar. 1, 2013, pp. e121-e128.

* cited by examiner

*Primary Examiner* — Karla A Dines
(74) *Attorney, Agent, or Firm* — Julie K. Staple; Dinsmore & Shohl LLP

(57) ABSTRACT

The present invention relates to a method and tools for extracting information on a compounds influence on a cellular phenotype. The method of the invention may be used as a very efficient procedure for testing the efficacy or resistance of single drugs or combinations of drugs on cells from individual patients. Thus, the methods may be useful for predicting efficacy of a drug on a given patient. The methods are also useful for testing of compounds for toxicity, identifying drug targets for known or novel compounds.

18 Claims, 6 Drawing Sheets

Screening of 2 individual patients

Patient 1: Spheroid growth is inhibited by 5FU and SN38 but not by Oxaliplatine, Leucovorine and Cetuximab Patient 2: Spheroid growth is inhibited by 5FU, SN38 and Oxaliplatin but not by Leucovorine and Cetuximab

IDENTIFYING COMPOUNDS MODIFYING A CELLULAR PHENOTYPE

FIELD OF INVENTION

The present invention relates to a method and tools for extracting information relating to the influence on a cellular phenotype or cellular property influenced by a compound or a combination of compounds. In particular, the method relates to a semi solid support that through multiple phase shifts allow loading of compounds and cells into the support and testing the influence of said compounds on the cellular system.

The method of the invention may be used as a very efficient procedure for testing or discovering the influence of a library of compounds on a cellular process, for example in connection with screening for new drugs, testing the efficacy or resistance of individual or combinations of compounds on patient cells, testing of compounds for toxicity, identifying drug targets for known or novel compounds. Other valuable uses of the method and technology of the invention will be apparent to the skilled person on the basis of the following disclosure.

BACKGROUND OF INVENTION

A large population of cancer patients do not respond effectively to the medical treatment offered to them as mono-therapy or adjuvant to surgery or radiation therapy (Ernst & Young report 2009: Lack of Drug responsiveness). In the late stages of cancer, a non-efficacious medical treatment can be devastating to the overall prognosis.

The concept of designing a specific treatment for the individual patient was boosted in the early days of the human genome project where it was believed that elucidation of the human genome would open for "fingerprinting" the disease progression and treatment sensitivity of individual patients. Genotyping of patients has proven successful in identification of responsive patients to single targeted drugs like Herceptin (HER-2/neu expression) and Erbitux/Tarceva (KRAS mutation). However, this has not been the case when trying to match specific combination therapies to individual patients.

Conducting cell functional analysis in-vitro on cells resected from a patient (e.g. a cancer patient) has shown that a highly significant correlation exists between drug resistance and patient outcome (Mechetner E, Brünner N, Parker R J. Scand J Gastroenterol. (2010) August 9; d'Amato et al. Ann. Surg. Oncol. (2009), 16, 2848).

In order to recapitulate the physiological and pathophysiological behavior of primary cancer cells in-vitro it is recognized that the cells should be grown in three-dimensional cultures (Sato et al. (2011), 141:1762-1772; Gastroenterology Godugu C, Patel A R, Desai U, Andey T, Sams A, et al. (2013), PLoS ONE 8(1): e53708).

SUMMARY OF INVENTION

Primary cells are susceptible, and should therefore only be subjected to as few handling steps as possible. Furthermore, access to primary cells is frequently limited and in order to avoid unnecessary loss of cell material as few handling steps as possible are desirable. Further to ensure that the primary cells show behaviour as close as possible to the behaviour of cells in-vivo it is preferred that the cells are tested shortly after removal from the intact organism (ex. patients).

The present invention provides methods useful for in-vitro testing of how cells react to a panel of compounds or composition of compounds, wherein the methods require very few handling steps. Furthermore, the methods allow testing a large panel of different compounds or combinations of compounds using only a limited number of cells. Thus, the methods are particularly useful for testing of cells susceptible to many handling steps or cells, with a limited supply.

Interestingly, the methods provides means for in-vitro testing the influence of a large panel of compounds/combinations of compounds in a manner, which recapitulates the physiological and pathophysiological behaviour of primary cells in-vitro by cultivating the cells in three-dimensional cultures.

Furthermore, the methods allow preparing arrays comprising compounds/combinations of compounds to be tested, wherein the arrays can be packaged and transported in a ready-to-use format. Thus, the methods may be very simple to perform for the user.

Furthermore, in preferred embodiments of the invention the methods ensure that cells appear in a narrow field of view allowing easy imaging-based testing.

Thus, in one aspect the invention provides methods of identifying a compound or a combination of compounds that modify a least one cellular phenotype, said method comprising the steps of:
 i) providing a plurality of library members, wherein each library member is a compound or a combinations of compounds;
 ii) providing a suspension of cells which may acquire said cellular phenotype;
 iii) providing a cell-compatible support, wherein the support reversible can change between a sol-state and a gel-state
 iv) providing an array containing a plurality of spaces
 v) adding said support in sol-state to the spaces of said array
 vi) adding library members to the spaces of said array, wherein at least two different library members are added to two different spaces,
 wherein steps v) and vi) may be performed simultaneously or sequentially in any order,
 vii) bringing the support to the gel-state;
 viii) contacting the spaces of said array with the suspension of cells, while the support is in the gel-state; and
 ix) bringing the support into the sol-state thereby allowing cells to flow into the support; and
 x) bringing the support to the gel-state thereby entrapping cells in the support; and
 xi) incubating the array under conditions allowing maintenance and/or growth of the cells
 xii) detecting the cellular phenotype in the cells,
 xiii) identifying library members modifying the cellular phenotype,
 thereby identifying a compound or a combination of compounds modifying said cellular phenotype.

The invention also provides methods of identifying a compound or a combination of compounds that modify a least one cellular phenotype, said methods comprising the steps of:
 i) providing a library containing a plurality of library members, wherein each library member is a compound or a combinations of compounds;
 ii) providing a suspension of cells which may acquire said cellular phenotype;

iii) providing a cell-compatible support, wherein the support reversible can change between a sol-state and a gel-state
iv) providing an array containing a plurality of spaces
v) adding said support in sol-state to the spaces of said array
vi) adding library members to the spaces of said array, wherein at least two different library members are added to two different spaces,
wherein steps v) and vi) may be performed simultaneously or sequentially in any order,
vii) bringing the support to the gel-state;
viii) contacting the spaces of said array with the suspension of cells, and
ix) bringing the support into the sol-state and
wherein steps viii) and ix) may be performed simultaneously or sequentially in any order,
x) bringing the support to the gel-state thereby entrapping cells in the support; and
xi) incubating the array under conditions allowing maintenance and/or growth of the cells
xii) detecting the cellular phenotype in the cells,
xiii) identifying library members modifying the cellular phenotype,
thereby identifying a compound or a combination of compounds modifying said cellular phenotype.

In another aspect the invention provides an array comprising a plurality of wells,
wherein one reservoir is connected to each of the wells; and
wherein each well comprises a cell-compatible support, wherein the support reversible can change between a sol-state and a gel-state; and
wherein at least 10 wells further comprises different library members; and
wherein each library member is a drug useful in treatment of cancer or a combination of drugs useful in treatment of cancer.

Such an array is particularly useful in the methods of the present invention.

It is also an aspect of the invention to provide methods of identifying a compound or a combination of compounds that modify a least one cellular phenotype, said method comprising the steps of:
i) providing an array comprising a plurality of spaces, wherein each space comprises a cell-compatible support, wherein the support reversible can change between a sol-state and a gel-state; and
wherein at least 2 spaces further comprises different library members; and
wherein each library member is a compound or a combination of compounds; and
wherein the support is in the gel-state;
ii) providing a suspension of cells which may acquire said cellular phenotype;
iii) contacting the spaces of said array with the suspension of cells; and
iv) bringing the support into the sol-state
wherein steps ii) and iii) may be performed simultaneously or sequentially in any order, thereby allowing cells to flow into the support; and
v) bringing the support to the gel-state thereby entrapping cells in the support; and
vi) incubating the array under conditions allowing maintenance and/or growth of the cells
vii) detecting the cellular phenotype in the cells,
viii) identifying library members modifying the cellular phenotype,
thereby identifying a compound or a combination of compounds modifying said cellular phenotype.

It is furthermore an aspect of the invention to provide methods of treatment of a clinical condition characterized by at least one cellular phenotype in an individual in need thereof, said method comprising the steps of
i) obtaining cells associated with said clinical condition from an individual suffering from said clinical condition;
ii) identifying a compound or a combination of compounds modifying said at least one cellular phenotype characterizing said clinical condition using one of the methods for identifying a compound or a combination of compounds according to the invention,
iii) Administering a therapeutically effective amount of said compound or combination of compounds to said individual,
thereby treating said clinical condition.

It is also an aspect of the invention to provide method for predicting the efficacy of treatment of a clinical condition with each of a plurality of library members in an individual suffering from said clinical condition, wherein the clinical condition is characterized by at least one cellular phenotype, and wherein each library member is a compound or a combinations of compounds said method comprising the steps of
i) providing a sample comprising cells associated with said clinical condition from an individual suffering from said clinical condition,
ii) determining whether said library members modify said cellular phenotype by using one of the methods for identifying a compound or a combination of compounds according to the invention,
wherein modification the of cellular phenotype by the library members is indicative of efficacy of treatment of the clinical condition in said individual.

It is also an aspect of the invention to provide a compound or a combination of compounds for treatment of a clinical condition in an individual in need thereof, wherein the clinical condition is associated with at least one cellular phenotype, and wherein the individual comprises cells associated with the clinical condition, in which said compound or combination of compounds are capable of modifying said cellular phenotype, wherein the compound or combination of compounds have been identified using one of the methods for identifying a compound or a combination of compounds according to the invention It is also an aspect of the invention to provide a kit-of-parts comprising an array according to the invention and information for performing the methods for identifying a compound or a combination of compounds according to the invention.

DEFINITIONS

Figure 1:
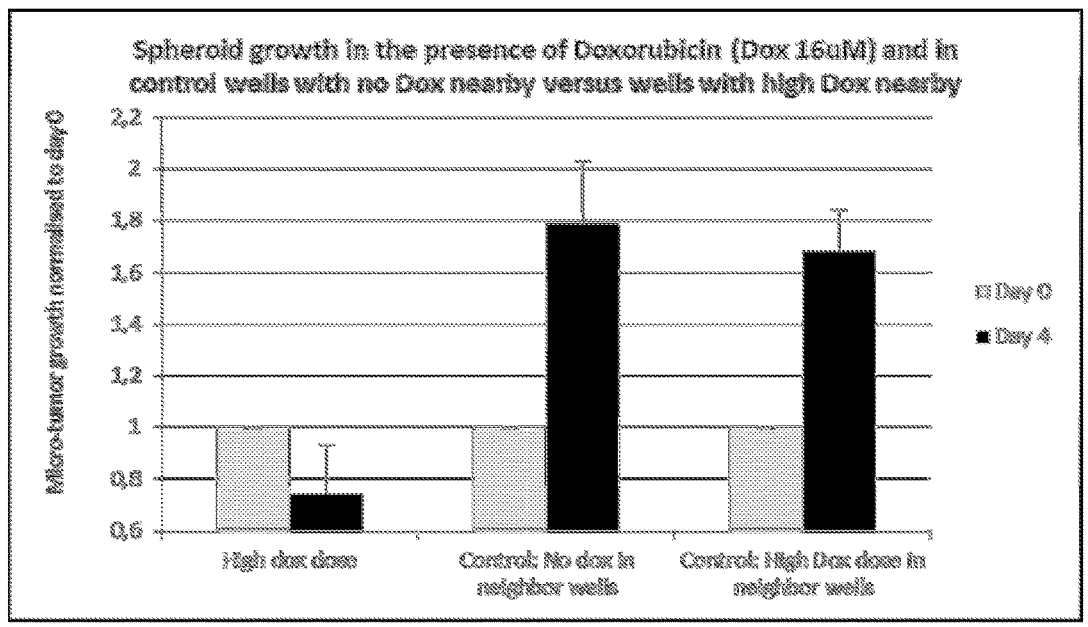
FIG. 1 shows micro-tumor growth in wells with high doxorubicin dose (left bar pair), control wells with no neighboring wells with doxorubicin (middle bar pair) and control wells with high doxorubicin adjacent (right bar pair). No spill over between wells is observed

The term "a" as used herein, can mean one or more, depending on the context in which it is used.

The term "library member" as used herein refers to either one compound or a combination of more than one compound. Each library member may thus be one compound or one specific combination of compounds.

The term "living cell" is used to indicate a cell which is considered living according to standard criteria for that particular type of cell. In general a cell is considered to be living, when normal membrane potential is maintained, cell membrane integrity is maintained and/or normal energy metabolism is maintained.

The term "sol-gel" as used herein refers to a support, which reversibly can shift between a "sol-state" and a "gel-state". It can be determined whether a support is in the "sol-state" or "gel-state" by placing the support in a conventional test tube. When the test tube is turned upside down, in the case where the interface (meniscus) between the support and air is deformed (including a case wherein the solution flows out from the test tube) due to the weight of the solution per se, the support is defined as being in the "sol state". On the other hand, in a case where the interface (meniscus) between the solution and air is not deformed due to the weight of the solution per se, even when the test tube is turned upside down, the above support is defined as being in the "gel state".

The term "approved drug" as used herein describes a compound or a combination of compounds that are approved by at least one national authority for use in treatment humans and/or animals.

The term "comprising" should be understood in an inclusive manner. Hence, by way of example, a composition comprising compound X, may comprise compound X and optionally additional compounds.

The term "plurality" should be understood as "at least two".

The term "library" should be understood as a collection of library members comprising at least 2 different library members.

The term "small organic molecules or compounds" refers herein to non-oligomeric, carbon containing compounds producible by chemical synthesis and generally having a size of less than 600 mass units.

The term "spheroid" as used herein refers to a plurality of cells attached to each other. Preferably, a spheroid comprises at least 10 cells, such as at least 50 cells, for example at least 100 cells attached to each other. Frequently, the spheroid is essentially ball-shaped; however, spheroids may also adopt other 3D shapes.

The term "treatment" as used herein may refer to curative or ameliorating treatment.

DETAILED DESCRIPTION OF THE INVENTION

Method of Identifying a Compound

In one aspect the present invention relates to methods for identifying a compound or a combination of compounds that modify a least one cellular phenotype. In general the methods comprises incubating a plurality of library members with cells, followed by detection of whether the library member modifies the cellular phenotype.

In general the methods comprise the steps of:
i) providing an array, which may be any of the arrays described herein below in the section "Array"; and
ii) providing a suspension of cells which may acquire said cellular phenotype, wherein said cells may be any of the cells described herein below in the section "Cells";
iii) contacting the spaces of said array with the suspension of cells; and
iv) bringing the support into the sol-state
  wherein steps iii) and iv) may be performed simultaneously or sequentially in any order, thereby allowing cells to flow into the support; and
v) bringing the support to the gel-state thereby entrapping cells in the support; and
vi) incubating the array under conditions allowing maintenance and/or growth of the cells
vii) detecting the cellular phenotype in the cells,
thereby identifying a compound or a combination of compounds modifying said cellular phenotype.

Thus in one embodiment steps iii) and iv) are performed in the following order:
iii) contacting the spaces of said array with the suspension of cells, while the support is in the gel state; and
iv) bringing the support into the sol-state.

The cellular phenotype may be any of the cellular phenotypes described herein below in the section "Cellular phenotype". In preferred embodiments of the invention, the cellular phenotype can be directly detected by visual inspection of the cells, for example by visual inspection using a microscope. Such cellular phenotypes may be for example be cell proliferation or cell death. As described in more detail below, the cells may be provided in the form of spheroids, and the cellular phenotype may be growth of said spheroids. Such growth can be directly detected by visual inspection.

Thus, in one embodiment the invention provides methods for identifying compounds or combination of compounds capable of inhibiting proliferation and/or growth of cells, said methods comprising the steps of:
i) providing an array, which may be any of the arrays described herein below in the section "Array"; and
ii) providing cells, which may be in the form of spheroids;
iii) contacting the spaces of said array with the cells; and
iv) bringing the support into the sol-state
  wherein steps iii) and iv) may be performed simultaneously or sequentially in any order, thereby allowing cells to flow into the support; and
v) bringing the support to the gel-state thereby entrapping cells in the support; and
vi) incubating the array under conditions allowing growth of the cells vii) detecting proliferation of cells and/or growth of the spheroids.

In one embodiment steps iii) and iv) are performed in the following order:
iii) contacting the spaces of said array with the suspension of cells, while the support is in the gel state; and
v) bringing the support into the sol-state.

As explained herein below the array comprises a plurality of spaces, wherein various spaces comprises different library members. Said library members may be any of the library members described in the section "Library" herein below.

In one embodiment the invention provides methods for identifying compounds or combination of compounds capable of inhibiting proliferation and/or growth of cells, said methods comprising the steps of:
i) providing an array, which may be any of the arrays described herein below in the section "Array", wherein the array comprises a cell-compatible support, wherein the support reversible can change between a sol-state and a gel-state at the sol-gel transition temperature; and
ii) providing cells, which may be in the form of spheroids; and
iii) contacting the spaces of said array with the cells;
iv) bringing the support into the sol-state by incubation at a temperature below the sol-gel transition temperature;
wherein step iii) and iv) may be performed simultaneously or sequentially on any order, thereby allowing cells to flow into the support; and
v) bringing the support to the gel-state by incubation at a temperature above the sol-gel transitions temperature, thereby entrapping cells in the support; and
vi) incubating the array under conditions allowing growth of the cells
vii) detecting proliferation of cells and/or growth of the spheroids.

As explained herein below the array comprises a plurality of spaces, wherein various spaces comprises different library members. Said library members may be any of the library members described in the section "Library" herein below.

Library

The methods of the present invention involve a step of providing a library of library members or providing an array comprising library members. The invention also relates to arrays comprising library members useful for the methods of the invention.

The library is a collection of library members. Each library member is a compound or a specific combination of compound(s).

The library or the array may preferably comprises at least 10, such as at least 20, for example at least 40, such as at least 50, for example at least 60, such as at least 70, for example at least 80, for example at least 90 different library members. Thus, at least 10, such as at least 20, for example at least 40, such as at least 50, for example at least 60, such as at least 70, for example at least 80, for example at least 90 library members may be provided and used with the methods of the invention. For example, in the range of 10 to 100, such as in the range of 20 to 100, for example in the range of 40 to 100, such as in the range of 50 to 100, for example in the range of 60 to 100, such as in the range of 70 to 100, for example, in the range of 10 to 80, such as in the range of 20 to 80, for example in the range of 40 to 80, such as in the range of 50 to 80, for example in the range of 10 to 50, such as in the range of 20 to 50 different library members are used with the methods of the invention.

The arrays to be used with the present invention comprise a plurality of spaces, which may comprise different library members. For example each space may comprise a different library member. It is also comprised within the invention that several spaces of an array may comprise the same library member, for example several spaces of an array may comprise the same library member in different concentration. Thus, an array may comprise the same library member in in the range of 1 to 20, such as in the range of 1 to 15, for example in the range of 1 to 10, such as in the range of 1 to 5 different concentrations. It is also comprised within the invention that the several spaces of the array may comprise the same library member in the same concentration.

As mentioned above each library member may be a compound or a combination of compounds. Said compounds may for example be small organic molecules, non-oligomeric, carbon containing compounds, or oligomers.

The oligomers may for example be peptides, glycopeptides, lipopeptides, nucleic acids (DNA or RNA), oligosaccharides, or proteins In certain embodiments of the present invention the library comprises or even consists of library members comprising drugs useful for treatment of a clinical condition. Thus, the library member may be a drug or a combination of drugs useful for treatment of a clinical condition. In particular, in embodiments of the invention, wherein the cells are cells associated with a clinical condition, then the library may comprise or even consist of library members comprising drug(s) useful for treatment of said clinical condition. For example in embodiments of the invention wherein the cells are cancer cells, for example the cells are primary cancer cells, then the library may comprise or consist of library members comprising drug(s) useful for treatment of cancer. Thus, said library members may be a drug or a combination of drugs useful for treatment of cancer.

Drugs useful for treatment of cancer includes chemotherapy compounds, cytotoxic compounds, sensitizing compounds, antibodies specifically targeting cancer cells, angiogenesis inhibitors, immune modulating compounds or hormones for hormone therapy. Cytotoxic compounds are compounds toxic to at least one cell type. Many conventional drugs for treatment of cancer are cytotoxic compounds. Sensitizing compounds are compounds, which may sensitize cancer cells to another treatment, for example to irradiation. Thus, sensitizing compounds may be compounds, which alone has no effect on cancer, but which in combination with another treatment can enhance the effect of said treatment.

Said drug useful for treatment of a clinical condition may be approved drugs. Non-limiting examples of drugs useful for treatment of cancer are described on http://www.cancer.gov/cancertopics/druginfo/alphalist. Thus, the drug useful for treatment of cancer may for example be selected from the group consisting of the following approved drugs. Thus, the library may comprise one or more library members comprising one or more drugs useful for treatment of cancer selected from the group consisting of drug Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bicalutamide, Bleomycin, Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Casodex (Bicalutamide), CeeNU (Lomustine), Ceritinib, Cerubidine, (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Herceptin (Trastuzumab), HPV Bivalent Vaccine, Recombinant, HPV Quadrivalent Vaccine, Recombinant, Hycamtin (Topotecan Hydrochloride), Hyper-CVAD, Ibritumomab Tiuxetan, Ibrutinib, ICE, Iclusig (Ponatinib Hydrochloride), Ifex (Ifosfamide), Ifosfamide, Ifosfamidum (Ifosfamide), Imatinib Mesylate, Imbruvica (Ibrutinib), Imiquimodlnlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), OEPA, OFF, OPPA, Oxaliplatin, Paclitaxel, Paclitaxel Albumin-stabilized Nanoparticle Formulation, PAD, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and 1131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VelP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zykadia (Ceritinib), and Zytiga (Abiraterone Acetate).

The library may also be a combinatorial library. Non-limiting examples of combinatorial libraries that may be used with the present invention and methods of producing such libraries are given in: Comprehensive Survey of Combinatorial Library Synthesis: 1998 Roland E. Dolle and Kingsley H. Nelson, Jr. J. Comb. Chem., 1999, pp 235-282; Comprehensive Survey of Combinatorial Library Synthesis: 1999 Roland E. Dolle J. Comb. Chem., 2000, pp 383-433; Comprehensive Survey of Combinatorial Library Synthesis: 2000 Roland E. Dolle J. Comb. Chem., 2001, pp 477-517; Comprehensive Survey of Combinatorial Library Synthesis: 2001 Roland E. Dolle J. Comb. Chem., 2002, pp 369-418 and Comprehensive Survey of Combinatorial Library Synthesis: 2002 Roland E. Dolle J. Comb. Chem., 2003, pp 693-753. The skilled person will appreciate that these protocols may be easily be adapted to specific need of a particular embodiment of the present invention.

In one embodiment, the library may comprise library members comprising or consisting of natural oligomers (oligomers of building blocks occurring in Nature) such as peptides, glycopeptides, lipopeptides, nucleic acids (DNA or RNA), or oligosaccharides. By way of example, a natural oligomer may be any peptide consisting of naturally occurring amino acid, even if said peptide comprises a sequence not present in nature. The libraries may also comprise polymers, such as polypeptides, or proteins, for example the library may comprise antibodies. The libraries may comprise different natural oligomers or the libraries may comprise only one kind of natural oligomer, for example the library may be a peptide library. In another embodiment, they can be unnatural oligomers (oligomers comprising one or more building blocks not occurring in Nature) such as chemically modified peptides, glycopeptides, nucleic acids (DNA or RNA), or, oligosaccharides, and the like. Said chemical modification may for example be the use of unnatural building blocks connected by the natural bond linking the units (for example, a peptide amide linkage), the use of natural building blocks with modified linking units (for example, oligoureas as discussed in Boeijen et al, 2001, J. Org. Chem., 66: 8454-8462; oligosulfonamides as discussed in Monnee et al, 2000, Tetrahedron Lett., 41: 7991-95), or combinations of these (for example, statine amides as discussed in Dolle et al, 2000, J. Comb. Chem., 2: 716-31.). Unnatural oligomers may comprise a mixture of naturally occurring and unnatural building blocks linked to each other by naturally occurring bonds. By way of example, the oligomer may comprise naturally occurring amino acids and unnatural building blocks linked by peptide bonds f.x. PNA or LNA. Thus, in one embodiment of the invention preferred oligomers comprise modified amino acids or amino acid (mimics). Other preferred unnatural oligomers include, for example oligoureas, poly azatides, aromatic C—C linked oligomers and aromatic C—N linked oligomers. Still other preferred oligomers comprise a mixture of natural and unnatural building blocks and natural and unnatural linking bonds. For example, the unnatural oligomer may be any of the oligomers mentioned in recent reviews see: Graven et al., 2001, J. Comb. Chem., 3: 441-52; St. Hilaire et al., 2000, Angew. Chem. Int. Ed. Engl., 39: 1162-79; James, 2001, Curr. Opin. Pharmacol., 1: 540-6; Marcaurelle et al., 2002, Curr. Opin. Chem. Biol., 6: 289-96; Breinbauer et al., 2002, Angew. Chem. Int. Ed. Engl., 41: 2879-90. The libraries of the invention may also comprise cyclic oligomers.

In yet another embodiment, the molecular entities may comprise non-oligomeric molecules such as peptidomimetics or other small organic molecules. Peptidomimetics are compounds that mimic the action of a peptidic messenger, such as bicyclic thiazolidine lactam peptidomimetics of L-proplyl-L-leucyl-glycinamide (Khalil et al, 1999, J. Med. Chem., 42: 2977-87). In a preferred embodiment of the invention, the library comprises or even more preferably consists of small organic molecules. Small organic molecules are non-oligomeric compounds of less than about 600 mass units containing any of a variety of possible functional groups and are the product of chemical synthesis, or isolated from nature, or isolated from nature and then chemically modified. Small organic compounds may for example be selected from the group consisting of alcohols, ethers, carboxylic acids, aryloxy, acyloxy, thiol, alkylthio, arylthio, heteroarylthio, sulphonyl, sulphoxy, amino, alkylamino, dialkylamino, acylamino, diacylamino, alkoxycarbonylamino, amides, alkyl, branched alkyl, aryl, heteroaryl, nitro, cyano, halogeno, silyloxy, keto, heterocycles, fused ring systems, fused heterocycles and mixtures thereof, wherein each of the aforementioned may be substituted independently on each position with one or more groups selected from the group consisting of —H, —OH, —SH, halogen, carboxyl, carbonyl, alkoxy, aryloxy, acyloxy, alkylthio, arylthio, heteroarylthio, sulphonyl, sulphoxy, amino, alkylamino, dialkylamino, acylamino, diacylamino, alkoxycarbonylamino, amides, alkyl, aryl, heteroaryl, nitro, cyano, halogeno, silyloxy, keto, heterocycles, fused ring systems, and fused heterocycles.

Non-limiting examples of small organic molecule libraries that may be used with the present invention and methods of producing them may for example be found in the reviews Thompson et al., 1996, Chem. Rev., 96: 555-600; Al-Obeidi et al., 1998, Mol. Biotechnol., 9: 205-23; Nefzi et al., 2001, Biopolymers, 60: 212-9; Dolle, 2002, J. Comb. Chem., 4: 369-418.

The library members may be added to the spaces of the array in their free form. However, it is also comprises within the invention that the library members may be linked to or associated with other compounds, when they are added to the spaces of the array. For example, the library members may be linked to or associated with particles, such as nano-particles. In one embodiment the library members are encapsulated in particles, e.g. encapsulated in nano-particles.

Cells

The methods of the present invention involve testing compounds for modifying a cellular phenotype. To this end, cells having said phenotype are provided or cells, which may acquire said phenotype are provided.

In preferred embodiments of the invention the cells are mammalian cells. For example the cells may be human cells.

The term "mammalian cell" is intended to indicate any cell of mammalian origin. The cell may be an established cell line, many of which are available from The American Type Culture Collection (ATCC, Virginia, USA) or a primary cell with a limited life span derived from a mammalian tissue, including tissues derived from a transgenic animal. The mammalin cells may also be newly established immortal cell lines derived from a mammalian tissue including transgenic tissues, or a hybrid cell or cell line derived by fusing different celltypes of mammalian origin e.g. hybridoma cell lines. The cells may optionally express one or more non-native gene products, e.g. receptors. The term "cell line" is meant to cover a group of cells, wherein the cells of that group are essentially genetically indistinguishable from each other. The cells of a cell line are thus all progeny of the same cell.

The cells may be cells capable of growing in suspension or they may be adherent cells. In one embodiment of the invention the cells have been genetically or otherwise modified in order to enhance their usability with the present invention. The modification may be stable or only transient or a mixture of both. For example, the cells may have been modified to contain one or more of the reporter systems, useful for detecting the cellular phenotype.

In a preferred embodiment of the invention the cells are primary cells. Primary cells are cells with a limited life span that preferably are derived from a mammalian tissue. The mammalian tissue may for example be a human tissue, such as healthy or diseased tissue. Thus, the cells may be cells resected from a human being.

In embodiments of the invention wherein the cells are human or animal primary cells, it is preferred that the methods of the invention are performed relatively short time after the cells have been obtained from said human or animal. Preferably the methods are performed within 2 weeks, such as within one week after obtaining the cells from said human or animal.

In one embodiment the cells are derived from a neoplastic tissue, for example a neoplastic tissue removed from a patient by surgery or neoplastic tissue removed from a patient as a biopsy. In particular, the cells may be primary cancer cells, such as cancer cells removed from a cancer patient by surgery or as a biopsy.

Said cancer cells may be cells of any cancer, for example any of the cancers described herein below in the section "Clinical condition". In particular, the cells may be cells of a cancer selected from the group consisting of melanoma, breast cancer, colon cancer, pancreas cancer, prostate cancer, head and neck cancer and lung cancer, Thus, the cells may be cancer cells removed from a cancer patient by surgery. The methods may then be used to identify a compound r a composition of compounds, which are useful in the continued treatment of said cancer patient.

The cells are usually provided in the form of a suspension of cells. Even in embodiments of the invention wherein the cells are adherent cells, they may be provided in the form of a suspension. In one preferred embodiment of the invention the cells are provided in the form of spheroids. Spheroids are a plurality of cells attached to each other. The cells may also be provided in the form of organoids.

The cells may also be hypertrophic cells, such as cardiac myocytes.

More than one type of cell may be provided and incubated in the array. For example, at least 2, such as at least 3, for example at 4, such as at least 5 different cell types may be provided an incubated in the support. Because the support generally is in the gel-state during incubation of the cells, the cells can grow in 3D and can thus form 3D structures. If different cell types are provides, said 3D structures may comprise different cell types, and thus they may even represent organoids. All different cell types may be obtained from one individual, or a mixture of cells from different individuals may be provided and incubated with the array. It is also comprised within the invention that a mixture of primary cells from one individual and cell lines are provided.

In one embodiment a mixture of endothial cells and cancer cells may be provided in order to test whether library members can affect angiogenesis. Said cells may be obtained from the same individual.

In other embodiments immune cells, for example T-cells may be provided in order to test whether library members can affect said immune cells. This may in particular be relevant in embodiments of the invention relating to methods for identifying library members for treatment of immune diseases.

Cellular Phenotype

The invention relates to methods of identifying compounds or combinations of compounds modulating a cellular phenotype. Thus, the compounds or combination of compounds may be compounds, which enhances or inhibits a cellular phenotype.

In a particularly preferred embodiment of the invention, the cellular phenotype is cell proliferation and cell death. In particular, in embodiments of the invention, wherein the cells are neoplastic cells, such as in embodiments of the invention wherein the cells are cancer cells, then the cellular phenotype may be cell proliferation. In such embodiments, the methods of the invention may be methods of identifying a compounds or combination of compounds capable of inhibiting cell proliferation, e.g. capable of inhibiting cancer cell proliferation.

Cell proliferation, such as cancer cell proliferation, may be determined in any of a number of different ways. For example, the number of cells after incubation in the presence of a library member may be counted. If the number of cells after incubation is less than the number of cells expected for the particular cell type after the given time of incubation, then the library member is capable of inhibiting cell proliferation. In particular the number of living cells after incubation may be counted. If the number of living cells after incubation is less than the number of living cells expected for the particular cell type after the given time of incubation, then the library member is capable of inhibiting cell proliferation. Thus, if the number of (living) cells after incubation is at the most 70%, such as at the most 60%, for example at the most 50%, such as at the most 40%, for example at the most 30%, such as at the most 20%, for example at the most 5% of the number of (living) cells expected for the particular cell type after the given time of incubation, then the library member is capable of inhibiting cell proliferation. The number of (living) cells expected may be determined by a control experiment performed under the same condition in the absence of any library member.

In particular it may be preferred that the library member is capable of completely inhibiting cell proliferation. In such cases cell proliferation may be determined by counting the number of cells before and after incubation with the library member. If the number of cells after incubation does not significantly exceed the number of cells before incubation, said library member is capable of completely inhibiting cell proliferation.

Cancer cell proliferation may also be determined by determining growth of a spheroid. As used herein the term "spheroid" designates a plurality of cells which are attached to each other. For example, the longest cross section of a spheroid after incubation may be determined. If the longest cross section after incubation is less than the expected longest cross section for the particular cell type after the given time of incubation, then the library member is capable of inhibiting cell proliferation. Alternatively, the area of the largest cross section of a spheroid after incubation may be determined. If the area of the largest cross section incubation is less than the expected area of the largest cross section for the particular cell type after the given time of incubation, then the library member is capable of inhibiting cell proliferation. Thus, if the longest cross section or the area of the largest cross section of a spheroid after incubation is at the most 70%, such as at the most 60%, for example at the most 50%, such as at the most 40%, for example at the most 30%, such as at the most 20%, for example at the most 5% of the expected longest cross section for the particular cell type after the given time of incubation, then the library member is capable of inhibiting cell proliferation. The expected longest cross section or the expected area of the largest cross section may be determined by a control experiment performed under the same condition in the absence of any library member. The term "longest cross section" as used herein refers to the length of the cross section of the spheroid, wherein said cross section is made at the place, where the spheroid is thickest. If the spheroid is completely circular, the longest cross section corresponds to the diameter.

In another embodiment of the invention the cellular phenotype may be inhibition of angiogenesis. This may in particular be the case in embodiments relating to methods for identifying a compound useful for treatment of cancer. In such embodiments, typically a mixture of cells is provided, wherein the mixture contains both cancer cells and endothelial cells. The cells are incubated under conditions allowing for angiogenesis in the absence of a library member, and library members reducing or inhibiting angiogenesis are identified.

In one embodiment the cellular phenotype may be mediated through interaction between cellular molecules, such as intracellular molecules. The cellular molecules may for example be components of a signal transduction pathway, and thus the cellular phenotype may be activation or repression of a signal transduction pathway. Such cellular phenotypes may be any of the cellular responses described in international patent applications WO 2005/116643 or WO2005/116656.

Examples of modulations of signal transduction pathway includes:
  Upregulation or downregulation of the level of a member of the pathway
  Relocalisation of a member of the pathway
  Complex formation between members of the pathway or between members of the pathway with other cellular compounds
  Enhanced or reduced transcription from genes regulated by the pathway
  Modification by for example phosphorylation of a member of the pathway
  Activation or inhibition of an enzyme of the pathway
  Degradation of a cellular compounds due to upregulation or downregulation of the pathway
  Altered secretion of a compound
  Change in ion-flux
  Morphological changes
  Change in viability The modulation of a signal transduction pathway can for example be monitored by measuring:
  the enzymatic activity of an enzyme being part of said signal transduction pathway
  the level of cyclic nucleotides, i.e. cAMP or cGMP
  the activity of transcription factors
  the level of specific proteins as quantified through standard proteomics techniques
  the level of inositol or lipid phosphates
  the level of phosphorylation of specific proteins as quantified through standard proteomics techniques
  the binding between two or more proteins or polypeptides
  the cellular localization of proteins or polypeptides Methods for monitoring modulation of a signal transduction pathway include the methods described in the section "Reporter system" and "Detectable output" in international patent applications WO 2005/116643 or WO2005/116656.

Support

The methods of the invention involves use of a cell compatible support, wherein the support reversible can change between a sol-state and a gel-state. Similarly, the arrays of the invention comprise such a support.

The term "cell compatible" as used herein refers to the support that when being in contact with cellular systems do not produce an adverse effect on the cells.

The support should preferably be able to support maintenance and/or growth of cells. A support is capable of supporting maintenance and/or growth of cells, if cells can reside in contact with said support and either stay alive and/or proliferate.

In particular, the support may be a support capable of supporting growth of 3D cell cultures. Typically 3D cultures are embedded in a polymer, for example a hydrogel like Matrigel (BD Matrigel™), PuraMatrix™ (3D Matrix Medical Technology), alginate or gelatin that upon a temperature change can shift between a sol-state and a gel-state without major disturbance to embedded cells.

It is preferred that the support is a temperature reversible gel, i.e. a gel, which reversible can change between the sol-state and the gel-state dependent on the temperature.

In particular it is preferred that the support is a cell compatible sol-gel.

Frequently, the support comprises one or more polymers. For example the sol-gel may comprise or consist of a hydrogel, e.g. a cell compatible hydrogel. The sol-gel may also be a mixture of different hydrogels.

A hydrogel according to the present invention generally consists of one or more polymers and a dispersion liquid. Said polymer(s) are herein referred to as "hydrogel polymers". The hydrogel polymer may be a polymer, which has a crosslinking or network structure, and has a property such that it can form a hydrogel by retaining water (in the inside thereof) on the basis of such a structure. The hydrogel may also comprise a combination of two or more different hydrogel polymers. Further, the term "hydrogel" refers to a gel which comprise, at least a crosslinked or network structure comprising a hydrogel polymer, and a dispersion liquid supported or retained by such a structure.

The "dispersion liquid" is typically an aqueous liquid useful for cultivation of cells. Thus, the dispersion liquid may be a cell cultivation medium. Cell cultivation media comprises the compounds required for maintenance and/or growth of cells, such as nutrients, hormones and growth factors. The cell cultivation medium should be compatible with the particular cell type used in the methods of the invention. The skilled person will be able to select a useful cell cultivation medium for a given type of cell. In particular, the support may be a sol-gel, which reversibly can switch between the "sol state", and the "gel state". Different factors may influence whether the sol-gel is in the "sol-state" or the "gel-state". Thus, for example the state of the sol-gel may be dependent on pH, temperature or the presence of specific ions.

In one embodiment the state of the sol-gel is dependent on pH. Thus, at a pH above a given pH the sol-gel may be in the gel-state, whereas at pH below a given pH the sol-gel may be in the sol-state. It is also possible that at a pH above a given pH the sol-gel may be in the sol-state, whereas at pH below a given pH the sol-gel may be in the sol-state. A non-limiting example of such a sol-gel includes Puramatrix gel available from BD Biosciences.

It is also comprised within the invention that the sol-gel may be in the gel-state, above a certain concentration of a compound, for example above a certain concentration of an ion. Said ion may for example be selected from the group consisting of $Ca^{2+}$ and $Na^+$.

In a preferred embodiment of the invention the sol-gel changes between the sol-state and the gel-state based on temperature. Thus, the sol-gel, may be a sol-gel, which reversibly can switch between the "sol state", and the "gel state" at the "sol-gel transition temperature".

The state of a sol-gel transition may preferably be determined as follows. 1 ml of a sol-gel in a sol state is poured into a test tube having an inside diameter of 1 cm, and is left standing for a predetermined time, e.g. 12 hours. Thereafter, when the test tube is turned upside down, in the case where the interface (meniscus) between the sol-gel and air is deformed (including a case wherein the solution flows out from the test tube) due to the weight of the solution per se, the above sol-gel is defined as a "sol state". On the other hand, in a case where the interface (meniscus) between the sol-gel and air is not deformed due to the weight of the solution per se, even when the test tube is turned upside down, the above sol-gel is defined as a "gell state".

The state of the sol-gel may be determined at particular temperatures, to determine the sol-gel transition temperature, at different pH or using other varying conditions.

The sol-gel transition temperature may be determined by performing above method while gradually increasing the above "predetermined temperature" (e.g., in 1 degrees C. increment), and determining the temperature at which the "sol state" is converted into the "gel state".

Determination and measurement of the "sol state," "gel state," and "sol-gel transition temperature" may also be carried out as mentioned below according to the definition and method described in a publication (H. Yoshioka et al., Journal of Macromolecular Science, A31(1), 113 (1994)).

That is, the dynamic elastic modulus of a sample at an observed frequency of 1 Hz is determined by gradually shifting the temperature from a low temperature side to a high temperature side (1 degrees C./1 min). In this measurement, the sol-gel transition temperature is defined as a temperature at which the storage elastic modulus (G', elastic term) of the sample exceeds the loss elastic modulus (G", viscous term). In general, the sol state is defined as a state in which G">G' is satisfied, and the gel state is defined as a state in which G"<G' is satisfied. A method of measuring elastic modulus, is e.g. described in: "Modern Industrial Chemistry" (Kindai Kyogyo Kagaku) No. 19, edited by Ryohei Oda, et al., Page 359, published by Asakura Shoten, 1985).

It is preferred that the support to be used with the present invention is a sol-gel with a sol-gel transition temperature in the range of 0 to 35° C., such as in the range 5 to 35° C., for example in the range of 10 to 35° C.

The sol-gel may for example be selected from the group consisting of gelatinous gels and copolymers.

The support may in particular be a sol-gel, and said sol-gel may for example be a hydrogel. The hydrogel usable for the support according to the present invention is not particularly limited, however preferably hydrogel exhibits the above-mentioned reversible sol-gel transition, such as a thermo reversible sol-gel transition (that is, preferably it has a sol-gel transition temperature).

Specific non-limiting examples of the hydrogel polymers includes e.g., polyalkylene-oxide block copolymer represented by block copolymers comprising polypropylene oxide portions and polyethylene oxide portions; etherified (or ether group-containing) celluloses such as methyl cellulose and hydroxypropyl cellulose; chitosan derivatives, e.g. such as described by K. R. Holme. et al. Macromolecules, 24, 3828 (1991).

The hydrogel polymer may preferably comprise a combination of plural hydrophobic blocks having a cloud point, and a hydrophilic block bonded thereto. The hydrophobic block may comprise or consist of hydrophobic monomers, whereas the hydrophilic block may comprise or consist of hydrophilic monomers. The cloud point based on the hydrophobic bonds preferably corresponds to the above-mentioned sol-gel transition temperature of the hydrogel.

More specifically, such a polymer having a cloud point may be one selected from the group consisting of: polypropylene oxide, copolymers comprising propylene oxide and another alkylene oxide, poly N-substituted acrylamide derivatives, poly N-substituted methacrylamide derivatives, copolymers comprising an N-substituted acrylamide derivative and an N-substituted methacrylamide derivative, polyvinyl methyl ether, and partially-acetylated product of polyvinyl alcohol.

Specific examples of the poly N-substituted acrylamide derivatives and poly N-substituted methacrylamide derivatives includes e.g. Poly-N-acryloyl piperidine, Poly-N-n-propyl methacrylamide, Poly-N-isopropyl acrylamide, Poly-N,N-diethyl acrylamide, Poly-N-isopropyl methacrylamide, Poly-N-cyclopropyl acrylamide, Poly-N-acryloyl pyrrolidine, Poly-N,N-ethyl methyl acrylamide, Poly-N-cyclopropyl methacrylamide or Poly-N-ethyl acrylamide.

Specific examples of the above hydrophilic monomer may include: N-vinyl pyrrolidone, vinyl pyridine, acrylamide, methacrylamide, N-methyl acrylamide, hydroxyethyl methacrylate, hydroxyethyl acrylate, hydroxymethyl methacrylate, hydroxymethyl acrylate, methacrylic acid and acrylic acid having an acidic group, and salts of these acids, vinyl sulfonic acid, styrenesulfonic acid, etc., and derivatives having a basic group such as N,N-dimethylaminoethyl methacrylate, N,N-diethylaminoethyl methacrylate, N,N-dimethylaminopropyl acrylamide, salts of these derivatives, etc. However, the hydrophilic monomer to be usable in the present invention is not restricted to these specific examples.

Specific examples of the above hydrophobic monomer may include: acrylate derivatives and methacrylate derivatives such as ethyl acrylate, methyl methacrylate, and glycidyl methacrylate; N-substituted alkyl methacrylamide derivatives such as N-n-butyl methacrylamide; vinyl chloride, acrylonitrile, styrene, vinyl acetate, etc. However, the hydrophobic monomer to be usable in the present invention is not restricted to these specific examples.

Specific examples of the hydrophilic block to be combined with (or bonded to) the above-mentioned block having a cloud point may include: methyl cellulose, dextran, polyethylene oxide, polyvinyl alcohol, poly N-vinyl pyrrolidone, polyvinyl pyridine, polyacrylamide, polymethacrylamide, poly N-methyl acrylamide, polyhydroxymethyl acrylate, polyacrylic acid, polymethacrylic acid, polyvinyl sulfonic acid, polystyrene sulfonic acid, and salts of these acids; poly N,N-dimethylaminoethyl methacrylate, poly N,N-diethylaminoethyl methacrylate, poly N,N-dimethylaminopropyl acrylamide, and salts of these, etc.

The hydrogel polymer may also comprise poly(ethylene glycol) (PEG), (poly (propylene oxide) and/or poly(ethylene oxide).

The hydrogel polymer may also comprise a natural polymer. As used herein the term "natural polymer" refers to naturally occurring polymers as well as polymers consisting of natural building blocks. Thus natural polymers may for example be polypeptides or polysaccharides. The hydrogel may consist of said natural polymer or polymer consisting of natural building blocks, or the hydrogel may comprise both synthetic polymer(s) and natural polymers, which optionally may be covalently linked to each other. Said natural polymer may for example be a polypeptide that mimic collagenase substrates, it may be extracellular matrices, fibrinogen, HA, alginate or chitosan.

The process for combining the above block having a cloud point with the hydrophilic block is not particularly limited. For example, it is preferred to obtain a block copolymer, or a graft copolymer, or a dendrimer-type copolymer containing these blocks.

A 10 percent-aqueous solution of the above hydrogel polymer may preferably show a viscosity of 10-3,000 Pa*s (10-3,000 centipoises), more preferably, 50-1,000 Pa*s (50-1,000 centipoises) at 5 degrees C.

In order to reduce or prevent cytotoxicity, it is preferred to use a hydrogel-polymer which can be converted into a gel state at a concentration of 20 percent or less (more preferably 15 percent or less, particularly 10 percent or less), wherein the concentration is {(polymer)/(polymer+dispersion liquid)}.

The support may also comprise additional components, for example components beneficial for maintenance and/or growth of cells. Thus, in embodiments of the invention where the support is a hydrogel, then in addition to the dispersion liquid and the hydrogel polymer, the support may also comprise additional components.

Said additional components may for example be antibiotics, ECM such as collagen or gelatin, hormones such as insulin and growth factors, and other cells or tissues capable of secreting same, or fatty acid derivatives such as prostaglandins.

The support may also be a co-polymer, for example a co-polymer selected from the group consisting of pluronic lecithin organogels and alginate hydrogels.

The cell-compatible hydrogel to be used with the invention may for example be a gelatinous gell. Examples of gelatinous gels include Matrigel™ and Puragel™.

Examples of useful cell-compatible hydrogels to be used with the invention and methods for designing same are described by Seliktar, 2012, Science, 336:1124-1128. Specific examples of useful hydrogels to be used with the present invention may be selected from the group consisting of h9e, Matrigel™, Puragel™, Pluronic, Puramatrix, and alginate hydrogel. Further examples of useful hydrogels are provided in Tables 1 and 2 below.

TABLE 1

| Characteristics | h9e | Puramatrix gel (BD Biosciences) [a] | Matrigel (BD Biosciences) [b] | Alginate hydrogel (ALgimatrix) [c] |
| --- | --- | --- | --- | --- |
| Material | Peptide (19 unit) | peptide (16 unit) | Reconstituted basement membrane extracted from EHS mouse tumor | Polysaccharides (dried sponge) |
| Porositys | 50-200 nm | 50-200 nm | 50-400 nm | 50-200 μm |
| Solution pH | Neutral | Acidic pH 3 | Various during the storage (acidic to physiological pH) | Dry |
| Gel trigger | Hydrogel could be triggered by directly mixing cell medium or solution containing $Ca^{2+}$, $Na^+$ (no pH or temperature adjustment) | Starts gel at pH higher than 4.5-5 (change medium at least 3 steps within first 30 min to equilibrate the sample to physiological pH). | Starts gel at temperature higher than 10° C. | Add gel firming buffer containing $Ca^{2+}$ |
| Cell encapsulation | Directly mix (pipette), cells suspended in cell medium before the peptide solution is added in a relaxed working environment. Cells are surrounded by medium and nanofibrils network during hydrogelation. | Directly mix (pipette, has to be very fast, within 1 min, to shorten the contact time of cell with acidic peptide solution); cells is isolated from medium and prepared in 10% sucrose solution before peptide solution is added | Directly mix with chilled pipette (need to chill everything before experiment because temperature is the trigger for gelation) | Immediately centrifuge after the firming buffer added (for better cell distribution) |
| Cell recovery | Pipette, dilute the hydrogel with cell medium 1:15 folds and centrifuge | Pipette to disturb the gel structure and centrifuge | Add cell recovery solution or lowing temperature or centrifugation to disrupt the gel matrix | Add dissolving buffer |

TABLE 2

| Material | Gel precursors | Crosslink mechanism | Degradation mechanism | Cells encapsulated |
|---|---|---|---|---|
| Chitosan | Macromer(s): chitosan grafted with lactic acid and methacrylate Initiator: APS/TEMDA | Covalent | Enzymatic (lysozyme) Hydrolytic[b] | Chondrocytes[12] |
|  | Macromer(s): chitosan-g-azidobenzoic acid and acryloyl-PEG-RGD | Covalent | Enzymatic (lysozyme) | Cardiomyocytes[98] |
| Alginate-co-Gelatin | Macromer(s): alginate dialdehyde and gelatin Crosslinking agent: Borax[c] | Covalent | Hydrolytic | Hepatocytes[90] |
| Styrenated gelatin | Macromer(s): styrenated gelatin Initiator: camphorquinone | Covalent | Enzymatic | Chondrocytes[72] |
| HA | Macromer(s): methacrylated HA Initiator: Irgacure 2959 | Covalent | Enzymatic (Hyaluronidase) | Valvular interstitial cells,[59] chondrocytes,[106, 134] fibroblasts[135] |
|  | Macromers(s): acrylated HA and PEG-(SH)$_4$ Other: triethanolamine (pH 8.0) | Covalent | Enzymatic (Hyaluronidase) | Human MSCs[26] |
|  | Macromer(s): thiol-modified HA and PEG diacrylate | Covalent | Enzymatic (Hyaluronidase)[b] | Adipocyte-stem cells,[109] chick dorsal root ganglia[110] |
| Chondroitin sulfate | Macromers(s): methacrylated chondroitin sulfate Initiator: Irgacure 2959 | Covalent | Enzymatic (Chondroitinase) | Chondrocytes[61, 62] |
| Synthetic ECM analogs | Macromer(s): thiol-modified HA or thiol-modified chondroitin sulfate, thiol-modified gelatin and PEG diacrylate | Covalent | Enzymatic[b] | Murine fibroblasts,[28] MSCs[113] |
| PEGylated fibrinogen | Macromers(s): fibrinogen-g-PEGacryloyl and PEG diacrylate Initiator: Irgacure 2959 | Covalent | Enzymatic (plasmin, MMPs) | Bone marrow stromal cells[85] |
| Self-assembled peptide gels | Macromer(s): self-assembling peptide Other: electrolyte solutions (e.g., sucrose, DMEM) | Physical | Dissolution or enzymatic[d] | Human MSCs,[75] preosteoblastes,[84] endothelial cells,[136] cardiomyocytes,[137] embryonic SCs[137] |
| Elastin-like polypeptide | Macromer(s): genetically engineered ELP Other: tissue transglutaminase and calcium chloride | Covalent | Enzymatic | Chondrocytes,[77] adipose-derived SCs[78] |
|  | Macromer(s): PLA-b-PEG-b-PLA dimethacrylate Initiator: Irgacure 2959 | Covalent | Hydrolytic | Osteoblasts,[39] neural precursor cells[138] |
| Poly(ethylene glycol) based | Macromer(s): PCL-b-PEG-b-PCL dimethacrylate Initiator: Irgacure 2959 | Covalent | Enzymatic (lipase) Hydrolytic | Chondrocytes[139] |

TABLE 2-continued

| Material | Gel precursors | Crosslink mechanism | Degradation mechanism | Cells encapsulated |
|---|---|---|---|---|
| | Macromer(s): PEG-(poly(glycerol succinic acidmethacrylate$_4$))$_2$ Initiator: Eosin-Y, NVP, triethanolamine | Covalent | Hydrolytic | Chondrocytes[37] |
| | Macromer(s): OPF and NVP Initiator: Irgacure 2959 | Covalent | Hydrolytic | Chondrocytes[126] |
| Polyfumarate based | Macromer(s): poly(lactide-co-ethylene oxide-co-fumarate) and MMP-diacrylate Initiator: APS/TEMDA | Covalent | Hydrolytic Enzymatic (MMPs) | Bone marrow stromal cells[133] |
| | Macromer(s): poly(ethylene glycol) di-[ethyl phosphatidyl (ethylene glycol) methacrylate] Initiator: Irgacure 2959 | Covalent | Hydrolytic | Goat MSCs[51] |
| Phosphoester | Macromer(s): poly(6-aminohexyl propylene phosphate)-acrylate Initiator: Irgacure 2959 | Covalent | Hydrolytic | Goat MSCs[125] |

$^b$Degradation may also occur via hydrolysis.
$^c$In addition to Borax, gel also forms crosslinks between amine groups on gelatin and dialdehyde groups on alginate.
$^d$Not confirmed.

APS: ammonium persulfate; TEMDA: N,N,N',N'-tetramethylethylenediamine; PEG: poly(ethylene glycol); HA: hyaluronic acid; Irgacure 2959: 2-hydroxy-1-[4-(hydroxyethoxy) phenol]-2-methyl-1-propanone; ECM: extracellular matrix; MSCs: mesenchymal stem cells; MMPs: metalloproteinases; DMEM: Dulbecco's modified Eagle's medium; ELP: Elastin-like peptides; PLA: poly(lactic acid); PCL: poly(δ-caprolactone); NVP: N-vinylpyrrolidone; OPF: oligo (polyethylene glycol) fumarate.

The standard handling of Matrigel is to keep it at low temperature (e.g. in the range of 0 to 8° C., for example at a temperature in the range of 0 to 5° C.) while adding cells. After the cells are embedded in the gel, the temperature is raised to in the range of 20° C. to 40° C., such as in the range of 22° C. to 37° C. and Matrigel will gel (enter gel-phase). The cells will now be allowed to grow in the 3D structure. Other hydrogels having a sol-gel transition temperature in the range of 10 to 35° C. may be handled in a similar manner.

Array

The arrays to be used with the present invention comprise a plurality of spaces, which each may comprise a support and a library member.

The arrays may also comprise spaces, which do not comprise support or library member. The array may also comprise spaces only comprising a support. Such spaces may be used as controls.

It is generally of importance that the array comprises discrete spaces, such that the support of one space cannot readily be mixed with the support of another space.

In one embodiment the array may comprise the support as spots or regions on a surface or a plated gel or a membrane. A spot or a region is a discrete space on said surface, where the support is positioned. The support is maintained within the space even when in the sol-state, e.g. due to surface tension. Thus, each spot may comprise specific library members, which are confined to said spot. Other components (e.g. the cell suspension) may be distributed over the entire array. In that manner, the cellular phenotype in response to different library members can be tested at the different spots, but at the same time, addition of the cell suspension does not require excessive pipetting, which may be harmful to cells. In such embodiments of the invention the volume of support placed in each space is very small. Thus, it should preferably be sufficiently small so that the support may be maintained within the space due to surface tension. Said surface could for example be a silicium wafer, a glass surface, a plastic surface or a gel. Plastic surface may for example be prepared from polystyrene, polycarbonate polypropylene, ethylene and/or teflon. Gels could be prepared from for example poly acrylamid or PEGA.

In preferred embodiments of the invention the array comprises spaces, which are separated from each other by physical barriers. Thus, for example the array may comprise a plurality of wells.

In a very preferred embodiment of the invention, the array comprises a plurality of compartments, which are each connected to a reservoir. Said plurality of compartments may for example be wells. Thus, each well may comprise specific compounds, e.g. library members, which are confined to said well, whereas as other components (e.g. the cell suspension) may be added to the reservoir and from there be distributed to each well. In that manner, the cellular phenotype in response to different library members can be tested in the different wells, but at the same time, addition of the cell suspension does not require excessive pipetting, which may be harmful to cells and/or result in loss of cells.

The array may comprise as many spaces, e.g. as many wells as desired. In general the array should comprise sufficient spaces (e.g. wells) so that each library member can be testing in a discrete space or well. Thus, the array may comprise least 10, such as at least 20, for example at least 40, such as at least 50, for example at least 60, such as at least 70, for example at least 80, for example at least 90 spaces or wells. For example, the array may comprise in the range of 10 to 100, such as in the range of 20 to 100, for example in the range of 40 to 100, such as in the range of 50 to 100, for example in the range of 60 to 100, such as in the range of 70 to 100 spaces or wells. Each space or well may comprise a different library member, wherein it is preferred that at least one space or well comprises no library member and thus can serve as control. It is also comprised within the invention that several spaces or wells comprise the same library member, but in different concentrations. In that manner, a dose-response curve may be established in order to determine whether the library member modifies the cellular response. It is preferred that at least two, such as at least 10, such as at least 20, for example at least 40, such as at least 50, for example at least 60, such as at least 70, for example at least 80, for example at least 90 spaces, wells or compartments comprises different library members.

One advantage of the present invention is that each space may be very small enabling easy testing of numerous library members optionally in varying concentrations. Thus, the array may comprise compartments or wells, wherein each compartment or well has a volume of at the most 50 µL, preferably at the most 40 µL, more preferably at the most 30 µL, for example at the most 20 µL, for example each compartment or well may have a volume in the range of 10 to 25 µL. The wells or compartments of the array may be of different size, but it is preferred that all wells or compartments of an array are of the same size.

One advantage of the methods of the present invention is that there is no spill over of library member from one space/well/compartment to the neighbouring spaces/wells/compartments, even though some components (e.g. the cell suspension) is added to the array in one or a few steps. This is even the case in embodiments of the invention where the wells or compartments are positioned in close vicinity of each other. Thus, the array may comprise at least two compartments or wells, which are separated by a physical barrier having a thickness of at the most 2 mm, such as at the most 1 mm. It is preferred that the distance between any compartment or well and its neighbouring compartment or well is at the most 2 mm, such as at the most 1 mm.

The array may be prepared from any useful material, such as from a plastic. For example the array may be a device that can be mass-produced by injection moulding.

In preferred embodiments of the invention, the array is prepared in a manner, so that it is known which library member is contained in which space/compartment/well. Also it is preferred that the concentration the library member in a given space/well/compartment is known. In that manner, after incubation the array may be inspected for spaces/wells/compartments, where the cellular phenotype has been modified, and then the compounds or combination of compounds modifying the cellular phenotype can be directly determined.

In particular the array may be prepared and supplied to a user in a manner, where the array is ready to use, so that the user should only add the cell suspension and incubate the array. After incubation the cells are inspected to determine the cellular phenotype and base on the knowledge of which space/compartment/well comprises which library member, the compounds or combination of compounds modifying the cellular phenotype may be determined.

It is however also comprised within the invention that each space/well/compartment comprises a random library member. After identification of a space/well/compartment comprising cells where the cellular phenotype has been modified, then the library member contained in said space/well/compartment may be determined. This may be done by mass spectrometry, NMR or any other method useful to determine the structure of a chemical compound. Methods of determining the structure of a compound are for example described in international patent application WO2005/116656 the section "Identification of compound" starting on p. 61.

The library may also have been prepared by parallel synthesis using a tag to enable identification of, what chemical synthesis steps the individual library member has been submitted to. This may for example be done by IRORI or radiofrequency tag. Alternatively, chemical synthesis steps may be performed in parallel to preparing a polymeric tag. Identification of the tag will thus provide knowledge of the compound.

Linking Library Members to the Support

The invention comprises use of arrays comprising a support comprising library members. Preferably, the spaces/wells/compartments of the array comprise different library members mixed with the support. Said library members may be evenly distributed in the support, however it is not a requirement that the the library members are evenly distributed. In some embodiments the library members are located more frequently at the bottom of the space/well/compartments, for example in embodiments, when the library members are encapsulated in particles.

This may be accomplished by mixing the support with the library member, while the support is in the sol-state. In principle this may be achieved in one of the following ways:
1) library member is added to a space/well/compartment
2) support in sol-state is added to space/well/compartment
3) support in sol-state and library members are mixed.
Alternatively, it may be done as follows:
4) support in sol-state is added to space/well/compartment
5) Optionally bringing the support to the gel-state
6) Library member is added to space/well/compartment
7) If support is in the gel-state, the support is brought to the sol-state
8) support in sol-state and library members are mixed.
Alternatively, it may be done as follows:
1) support in the sol-state is mixed with the library member
2) the mixture is added to space/well/compartment Depending on the nature of the support, the support may be brought into the sol-state by a number of methods. In embodiments of the invention, wherein the support is a sol-gel with a transition temperature, then this is accomplished by transferring the array to a temperature, wherein the sol-gel is in the sol-state. Typically, this is accomplished by transferring the array to a temperature below the transition temperature of said sol-gel.

In preferred embodiments of the present invention the library members are added to the support while the support is in the sol-state. The library members will be passively linked to the support and subsequently affecting the cellular phenotype after passive diffusion.

In yet another preferred embodiment library members is encapsulated into particulate nano-structures like e.g. small molecules, peptides, proteins, nucleotides (for reviews see e.g. Nagarwal et al. 2009, J Control. Release 136, 2-13; Gasco 2007, Adv. Drug Delivery Rev. 59, 377-378) these structures are inserted into the support, while the support is being in its sol-state before the addition of cells. The compound(s) will in most cases have to be released from the nano-structures in order to exert their biological activity. Such release can occur in the extra-cellular space or after entry of the nano-structures into the cells. Such release can be controlled by a number of different stimuli e.g. light, pH change, temperature, ultra sound, enzymes, and change in redox potential.

In yet another preferred embodiment the library members will be covalently linked to the support.

In preferred embodiments of the invention specific library members are positioned in the array in a manner where the location of the specific space describes the identity of the library member.

In another embodiment the array is designed such that the cellular phenotype can be monitored using an optical device like a microscope. Further, the array is designed such that the cells are added in suspension and the cells will distribute to each of multiple spaces of the array holding a specific library member.

Incubating Array

The methods of the invention involve a step of incubating an array, which may be any of the arrays described herein above with cells. After incubation the array is inspected to identify which spaces/wells/compartments comprise cells, where the cellular phenotype has been modified. Once the spaces/wells/compartments have been identified, then the library members contained in said spaces/wells/compartments can be identified.

Typically, the cells are provided in the form of a suspension. Even if said cells do not naturally grow in a suspension, then for the purposes of the present invention, the cells are generally added in the form of a suspension. The skilled person is well aware of conventional methods for preparing cell suspensions. For example cell suspensions may be prepared by enzymatic treatment and/or physical separation. For example the cell suspension may be prepared by physical separation followed by treatment with one or more enzymes capable of degrading components involved in cellular attachment. Said enzymes may for example be proteolytic enzymes, for example trypsin or collagenase. The cell suspension may comprise cells more or less completely detached from each other, or at least some of the cells may be in the form of spheroids. For example, at least 70%, such as at least 80%, for example at least 90%, such as all of cells may be in the form of spheroids.

The cell suspension is then added to the array, wherein the support (e.g. the hydrogel) is in the gel-state (e.g. the hydrogel is in the gel-phase). One advantage of the present invention is that the cells may be added to the array in only one or a few steps, such as in at the most 10 steps, preferably in at the most 5 steps, such as in at the most 2 steps, for example in only one step. This is feasible, because the library members are contained within the support in the gel-state, which prevents spill over from one space to another.

In embodiments of the invention wherein the array comprises multiple compartments or well connected to one reservoir, then the cells are simply added to said reservoir.

Typically, the cells are allowed to settle into the wells/compartments, and excess liquid may be removed. I.e. the cells are may be allowed to settle into the wells/compartments by gravity, and the liquid of the cell suspension in the reservoir may be removed.

Once the cells are in contact with the support in the spaces/wells/compartments, e.g. after the cells have settled in the wells/compartments, then the support is brought to the sol-state. Depending on the nature of the support, the support may be brought into the sol-state by a number of methods. In embodiments of the invention, wherein the support is a sol-gel with a transition temperature, then this is accomplished by transferring the array to a temperature, wherein the sol-gel is in the sol-state. Typically, this is accomplished by transferring the array to a temperature below the transition temperature of said sol-gel.

Once the support is in the sol-state, the cells are allowed to flow into the support. This may be accomplished by gravity. When the cells are in a desired position the support is brought into the gel-state thereby entrapping the cells in the support. In particular it is preferred that the cells are allowed to settle in a narrow field, which may facilitate monitoring the cells using an optical device like a microscope. Thus, preferably, the cells are allowed to settle in a field sufficiently narrow to allow inspection of the cells with a microscope, wherein essentially all cells can be inspected without the need to change focus of said microscope. In a preferred embodiment of the invention, the cells are allowed to settle at the bottom of the well/compartment. Thus, at least 70%, such as at least 80%, for example at least 90%, such as essentially all of the cells are allowed to settle at the bottom of the well/compartment, where after the support is brought into the gel-state. If cells are allowed to settle at the bottom of the well/compartment, this may facilitate monitoring the cells using an optical device like a microscope.

Depending on the nature of the support, the support may be brought into the gel-state by a number of methods. In embodiments of the invention, wherein the support is a sol-gel with a transition temperature, then this is accomplished by transferring the array to a temperature, wherein the sol-gel is in the gel state. Typically, this is accomplished by transferring the array to a temperature above the transition temperature of said sol-gel. Said temperature is preferably also a temperature allowing maintenance and/or growth of cells. Thus, it is preferred that said temperature is in the range of 30 to 40° C., such as in the range of 35 to 38° C., for example around 37° C. Said temperatures are in particular useful, when the cells are mammalian cells, such as human cells.

The array with the cells in then allowed to incubate of a time sufficient to monitor, whether the library member can modify the cellular phenotype. Typically, the array with the cells is allowed to incubate for in the range to 1 to 20 days, such as in the range of 2 to 10 days. In embodiments of the invention where the cellular phenotype is cell proliferation, then typically, the array with the cells is allowed to incubate for in the range to 5 to 20 days, such as in the range of 5 to 10 days.

The condition for incubation depends on the specific cells. Thus the incubation should be performed under conditions allowing maintenance and/or growth of the particular type of cells. For a large number of mammalian cells, such conditions comprise high humidity, preferably close to 100%, approximately 5% $CO_2$ and around 37° C.

In general the arrays contain a hydrogel comprising a dispersion liquid, which is a cell cultivation medium. Thus, additional cell cultivation medium may not be required.

After incubation the array may be investigated for spaces/wells/compartments comprising cells, where the cellular phenotype has been modified, and the library member of these spaces/cells/compartments may be identified.

Clinical Condition

In some embodiments the invention relates to methods for treatment of a clinical condition. In particular, the methods of the invention are useful for determining a useful treatment regime for a particular individual.

Thus, cells obtained from an individual may be tested against a number of library members in order to identify a library member, which is useful for treatment of said particular individual.

By way of example, if an individual suffers from cancer, then cancer cells may be obtained from said individual. A library of drugs and combinations of drugs useful in cancer treatment may then be added to the array, and a drug or a combination of drugs inhibiting or at least reducing proliferation of said cancer cells may be determined.

Said individual may then be treated with said drug or combination of drugs.

In some embodiment within the invention relates to methods for predicting the efficacy of a treatment of a clinical condition. In particular, the methods of the invention are useful for determining whether a treatment regime may be useful for a particular individual.

Thus, cells obtained from an individual may be tested against a number of library members in order to test whether any of the library members may be useful for treatment of said particular individual.

The methods of the invention may thus comprise testing cells from an individual suffering from a clinical condition against a number of library members in order to identify library members that can reduce or inhibit a cellular phenotype associated with the clinical condition. Thus, drugs and combinations of drugs useful in treatment of said clinical condition may be added to the array, and it may be tested if any of the drugs or combinations of drugs are able to inhibit or at least reduce a cellular phenotype associated with the clinical condition. If none of the library members are able to inhibit or at least reduce the cellular phenotype, then it is predicted that treatment with any of the library members have little efficacy and another treatment should be sought. If one the other hand one or more library members are able to inhibit or at least reduce the cellular phenotype, then said library members may be selected for treatment of said individual.

By way of example, if an individual suffers from cancer, then cancer cells may be obtained from said individual. A library of drugs and combinations of drugs useful in cancer treatment may then be added to the array, and it may be tested if any of the drugs or combinations of drugs are able to inhibit or at least reduce proliferation of said cancer cells. If none of the library members are able to inhibit or at least reduce proliferation of said cancer cells, then it is predicted that treatment with any of the library members have little efficacy and another treatment should be sought. If one the other hand one or more library members are able to inhibit or at least reduce proliferation of said cancer cells, then said library members may be selected for treatment of said individual.

In one embodiment the invention relates to a compound or a combination of compounds for treatment of a clinical condition in an individual in need thereof, wherein the clinical condition is associated with at least one cellular phenotype, and wherein the individual comprises cells associated with the clinical condition, in which said compound or combination of compounds are capable of modifying said cellular phenotype, wherein the compound or combination of compounds have been identified by the methods of the invention.

Thus, the invention may relate to a compound or a combination of compounds for treatment of a clinical condition in an individual in need thereof, wherein the clinical condition is associated with at least one cellular phenotype, and wherein the individual comprises cells associated with the clinical condition, in which said compound or combination of compounds are capable of modifying said cellular phenotype, wherein the compound or combination of compounds have been identified by the method comprising the steps of i) providing an array comprising a plurality of spaces, wherein each space comprises a cell-compatible support, wherein the support reversible can change between a sol-state and a gel-state; and
wherein at least 2 spaces further comprises different library members; and
wherein each library member is a drug or a combination of drugs useful in the treatment of said clinical condition,
and wherein the support is in the gel-state
ii) providing a suspension of cells obtained from said individual, wherein the cells are associated with the clinical condition and the cells may acquire the cellular phenotype;
iii) bringing the support to the gel-state;
iv) contacting the spaces of said array with the suspension of cells; and
v) bringing the support into the sol-state
wherein steps iv) and v) may be performed simultaneously or sequentially in any order, thereby allowing cells to flow into the support; and
vi) bringing the support to the gel-state thereby entrapping cells in the support; and
vii) incubating the array under conditions allowing maintenance and/or growth of the cells
viii) detecting the cellular phenotype in the cells,
ix) identifying library members modifying the cellular phenotype.

In one embodiment of the steps iv) and v) are performed in the following order:
i) contacting the spaces of said array with the suspension of cells, while the support is in the gel state; and
ii) bringing the support into the sol-state.

In one embodiment, the invention may relate to a drug or a combination of drugs for treatment of cancer in an individual in need thereof, wherein the drug or combination of drugs have been identified by the method comprising the steps of
i) providing an array comprising a plurality of spaces, wherein each space comprises a cell-compatible support, wherein the support reversible can change between a sol-state and a gel-state; and
wherein at least 2 spaces further comprises different library members; and
wherein each library member is a drug or a combination of drugs useful in the treatment of cancer,
and wherein the support is in the gel-state
ii) providing a suspension of cancer cells obtained from said individual;
iii) bringing the support to the gel-state;
iv) contacting the spaces of said array with the suspension of cells; and v) bringing the support into the sol-state
wherein steps iv) and v) may be performed simultaneously or sequentially in any order, thereby allowing cells to flow into the support; and
vi) bringing the support to the gel-state thereby entrapping cells in the support; and
vii) incubating the array under conditions allowing growth of the cells
viii) detecting cancer cell proliferation,
ix) identifying library members modifying cancer cell proliferation.

In one embodiment the steps iv) and v) are performed in the following order:
i) contacting the spaces of said array with the suspension of cells, while the support is in the gel state; and
ii) bringing the support into the sol-state.

It is also an aspect of the invention to provide a method for predicting the efficacy of treatment of a cancer in an individual in need thereof, wherein the method comprises
i) providing cancer cells from said individual, which optionally may be in the form of spheroids;
ii) providing an array, which may be any of the arrays described herein below in the section "Array", wherein the array comprises a cell-compatible support, wherein the support reversible can change between a sol-state and a gel-state at the sol-gel transition temperature and wherein the array comprises a library of library members, wherein the library members are drugs useful in cancer treatment or a combination of drugs useful in cancer treatment; and
iii) contacting the spaces of said array with the cells;
iv) bringing the support into the sol-state by incubation at a temperature below the sol-gel transition temperature;
wherein step iii) and iv) may be performed simultaneously or sequentially on any order, thereby allowing cells to flow into the support; and
v) bringing the support to the gel-state by incubation at a temperature above the sol-gel transitions temperature, thereby entrapping cells in the support; and
vi) incubating the array under conditions allowing growth of cancer cells
vii) detecting proliferation of cells and/or growth of the spheroids.
viii) identifying a drug useful in cancer treatment or a combination of drugs useful in cancer treatment, which is capable of inhibiting proliferation of said cancer cells and/or growth of said spheroids,
wherein said drug or combination of drugs are useful for treatment of cancer in said individual.

As explained above, said methods involve use of cells obtained from an individual suffering from a clinical condition. In particular, it is preferred that the cells are causative of said clinical condition. Thus, by way of example, if the clinical condition is cancer, then preferably the cells are cancer cells, such as primary cancer cells of said individual. Such primary cancer cells may be obtained after surgery or by biopsy. It is also comprised within the invention that a mixture of cells may be provided. In such cases it is preferred that at least one type of cells are causative of the clinical conditions, and at least one other type of cell is involved in the clinical condition.

If the clinical condition is a condition caused by or involving neoplastic cell growth, then the cells preferably are neoplastic cells.

Thus, the clinical condition may be a condition caused by or involving neoplastic cell growth, such as benign tumors, cancer, inflammatory disease and immunological disease, autoimmune disease, or infectious diseases.

In a preferred embodiment of the invention, the clinical condition is cancer. Cancer (malignant neoplasm) is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not.

A non-limiting group of cancers given as examples of cancers that may be treated, managed and/or where treatment efficacy may be prediction by the methods of the present invention include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

For example the cancer may be selected from the group consisting of melanoma, breast cancer, colon cancer, pancreas cancer, prostate cancer, head and neck cancer and lung cancer.

EXAMPLES

The invention is further illustrated by the following examples, which should not be construed as limiting for the invention.

Throughout the examples the term "Fluid" is used to indicate that the support is in the sol-state, whereas the term "Solid" is used to indicate that the support is in the gel-state.

Example 1

Loading of Array with Chemo-Therapeutic Compounds "Freely" Distributed in the Support as Single Compounds and in Combinations at Various Concentrations and Ratios Materials and Solutions:
Support: Matrigel® available from BD Biosciences.
Arrays: Micro slide format arrays with 96 individual wells surrounded by a common reservoir. Each well has a volume of 20 µL and the distance between neighboring wells was 1 mm.
Chemo therapeutic compounds (Irinitecan, Oxaliplatin, Leucovorin, 5FU, Cetuximab)
Cooling device for keeping 5° C.
Procedure:
Compounds, Matrigel® and arrays are kept at 5° C. (cooling device) throughout the process when not in the freezer.
1. Compounds were diluted in Matrigel® (Fluid) as single compounds and/or in combinations equal to standard treatment regimens of patients with colorectal cancer.
2. Matrigel® with compounds were added to individual wells of the arrays (Fluid)
3. Arrays were centrifuged 10 min at 3000 RPM (cold)
4. Arrays were stored at −18° C. (Solid)—ready for use

Example 2

Loading of Arrays with Test Compounds Imbedded in Thermo Sensitive Nano-Particles Distributed in Matrigel; for Release Upon Demand Materials and Solutions:
Nano-particles containing chemo therapeutic compounds
Support: Matrigel® available from BD Biosciences,
Arrays: Micro slide format array with 96 individual wells surrounded by a common reservoir as described in Example 1
Cooling device for keeping 5° C.
Procedure:
Nano-particles, Matrigel® and arrays were kept at 5° C. (cooling block) throughout the process when not in the freezer.
1. Compound containing nano-particles were diluted in Matrigel® (fluid).
2. Matrigel containing the nano-particles (from above point 1) were added to individual wells of the array
3. The arrays were centrifuged 10 min at 3000 RPM (cold)
4. The arrays were stored at −18° C. for 24 hrs. (solid)

Example 3

No spill over occurs between wells because the support is solid when cells are added to the reservoir Materials and Solutions:
Support: Matrigel® available from BD Biosciences
Arrays: Micro slide format arrays with 96 individual wells surrounded by a common reservoir as described in Example 1
Chemo therapeutic compound: Doxorubicin
Cooling device for keeping 5° C.
Procedure:
Compounds, Matrigel® and arrays are kept at 5° C. (cooling device) throughout the process when not in the freezer.
1. Doxorubicin was diluted in Matrigel® (Fluid)
2. Matrigel® with Doxorubicin was added to individual wells of the arrays (Fluid)
3. The array was centrifuged 10 min at 3000 RPM (cold)
4. The array was stored at −18° C. for 24 hrs. (Solid)
1. Tumor tissue from patient was prepared to form a population of small individual micro-tumors (spheroids)
2. Micro-tumors were suspended in cold STEM media
3. The array was taken directly from freezer and placed on the cooling device (solid)
4. The micro tumor suspension was added to the reservoir of the array
1. The array was left for 7 min. to allow cells to distribute and settle into individual wells of the array
5. STEM media was gently removed from reservoir—leaving the micro tumors in the wells
6. The array was moved to refrigerator (5° C.) and left for 30 min to allow Matrigel® to liquefy and the cells to settle at the bottom of the array (fluid)
7. Hereafter the array was incubated at 37° C. for 1 hr. to allow the Matrigel® to solidify and fix the cells in a certain position (solid)
8. The array with micro-tumors positioned at the bottom was imaged at an automated microscope
9. Array was incubated at 37° C. and images were acquired every day for 10 days and micro-tumor growth (and inhibition of growth) was measured by quantifying the area of the micro-tumors.

As shown in FIG. 1 then the presence of a cytotoxic agent (doxorubicin) in the neighboring well had no significant effect on spheroid tumour growth. Accordingly, it can be concluded that there is no spill over between the wells.

Example 4

Screening of Compounds Distributed in Support; Matrigel®

Materials and Solutions:
Array prepared as described in Example 1
STEM media: DMEM/F12 w. 15% Hepes (Gibco 11330-032), StemPro hESC SFM growth supplement (50×): 1×
BSA 25%, Gibco A10008-01: 1.8%, FGF-basic (10 ug/ml): 8 ng/ml, 2-Mercaptoethanol Gibco 21985 (55 mM): 0.1 mM, Penicillin/streptomycin 200 U/ml/200 ug/ml (=2× usual conc.), Gentamycin Sigma G1272: 1:100 (=2× usual conc.), Amphotericin (fungicide): 1:100 (=1× usual conc.), Hepes 15 mM
Cooling device for keeping 5° C.
Incubator, 37° C. (CO2, 99% humidity for cell culture)
Procedure:
1. Tumor tissue from patient was prepared to form a population of small individual micro-tumors (spheroids)
2. Micro-tumors were suspended in cold STEM media
3. The array was taken directly from freezer and placed on the cooling device (solid)
4. 3 ml micro tumor suspension was added to the reservoir of the array and the array was left for 7 min. to allow cells to distribute and settle into individual wells of the array
5. STEM media was gently removed from reservoir—leaving the micro tumors in the wells
6. The array was moved to refrigerator (5° C.) and left for 30 min to allow Matrigel® to liquefy and the cells to settle at the bottom of the array (fluid)
7. Hereafter the array was incubated at 37° C. for 1 hr. to allow the Matrigel® to solidify and entrap the cells in a certain position (solid)

8. The array with micro-tumors positioned at the bottom was imaged at an automated microscope
9. Images were acquired every day for 10 days and micro-tumor growth (and inhibition of growth) was measured by quantifying the area of the micro-tumors.

Figure 2:
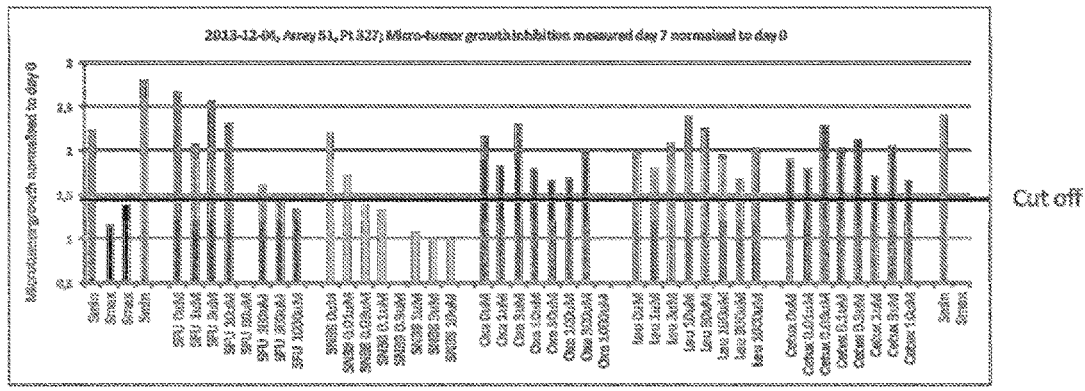
FIG. 2 shows chemo-sensitivity screening. A) shows chemo-sensitivity screening on micro-tumors from two different patients; Growth inhibition by a panel of standard chemo-therapies in increasing concentrations is tested. In patient 1 cancer cell proliferation is inhibited by 5FU and SN38, but not by Oxaliplatine, Leucovorine and Cetuximab. In patient 2 cancer cell proliferation is inhibited by 5FU, SN38 and Oxaliplatin, but not by Leucovorine and Cetuximab. B) shows chemo-sensitivity screening on cancer cell spheroids from three different cancer patients (upper panel: patient with low sensitivity to tested drugs; middle panel: patient with moderate sensitivity to tested drugs; lower panel: patient with high sensitivity to tested drugs). C) shows CT scanning of the patient showing moderate sensitivity after treatment with compounds predicted to be effective.
Figure 2:
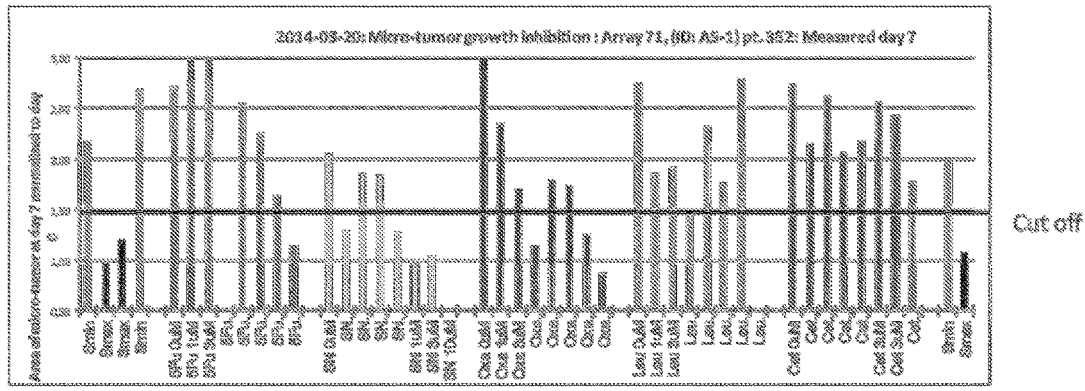
Figure 2B:
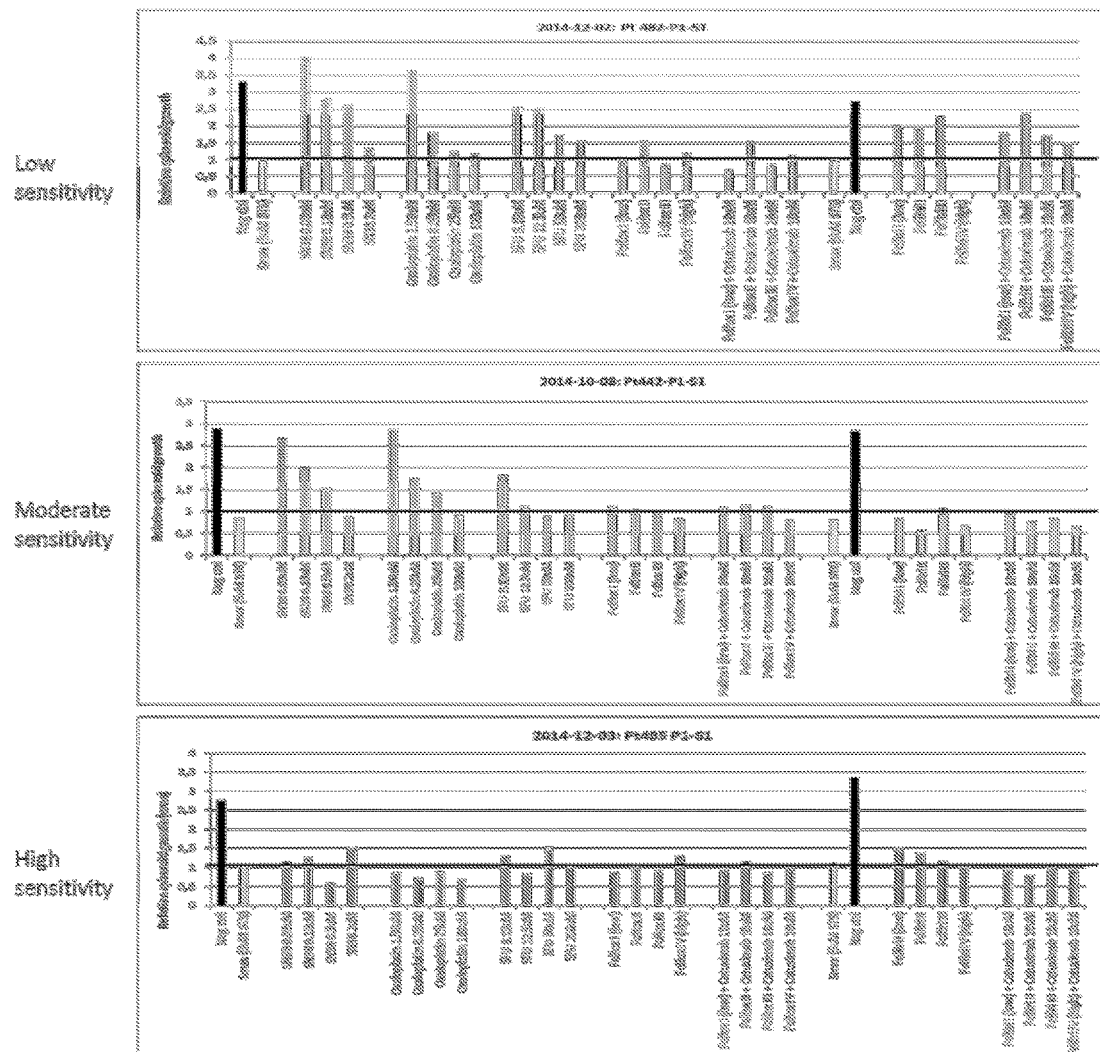

Examples of results achieved are shown in FIGS. 2a and 2b, which shows growth inhibition by a panel of standard chemo-therapies in increasing concentrations. In general cancer cell proliferation as evidenced by spheroid (micro-tumour) growth was considered inhibited if the spheroid had grown to less than 1.5× the original size after 7 days of incubation at least at the highest concentrations tested. In FIG. 2a, in patient 1 cancer cell proliferation is inhibited by 5FU and SN38, but not by Oxaliplatine, Leucovorine and Cetuximab. In patient 2 cancer cell proliferation is inhibited by 5FU, SN38 and Oxaliplatin, but not by Leucovorine and Cetuximab. Thus, it may be advantageous to treat patient 1 with 5FU and/or SN38, but not with Oxaliplatine, Leucovorine or Cetuximab. Similarly, it may be advantageus to treat patient 2 with 5FU, SN38 and/or Oxaliplatin, but not with Leucovorine and Cetuximab.

In FIG. 2b cell of three different patients show low, moderate and high sensitivity respectively, towards a panel of standard treatments as mono and combination therapy. The cells of the low sensitive patient responds poorly to both single compounds and compounds in combination whereas the cells of the high sensitive patient respond well to both single compounds and combination therapy. The cells of the moderate sensitive patient show little sensitivity towards single compounds but good response to combination therapies.

Figure 2C:
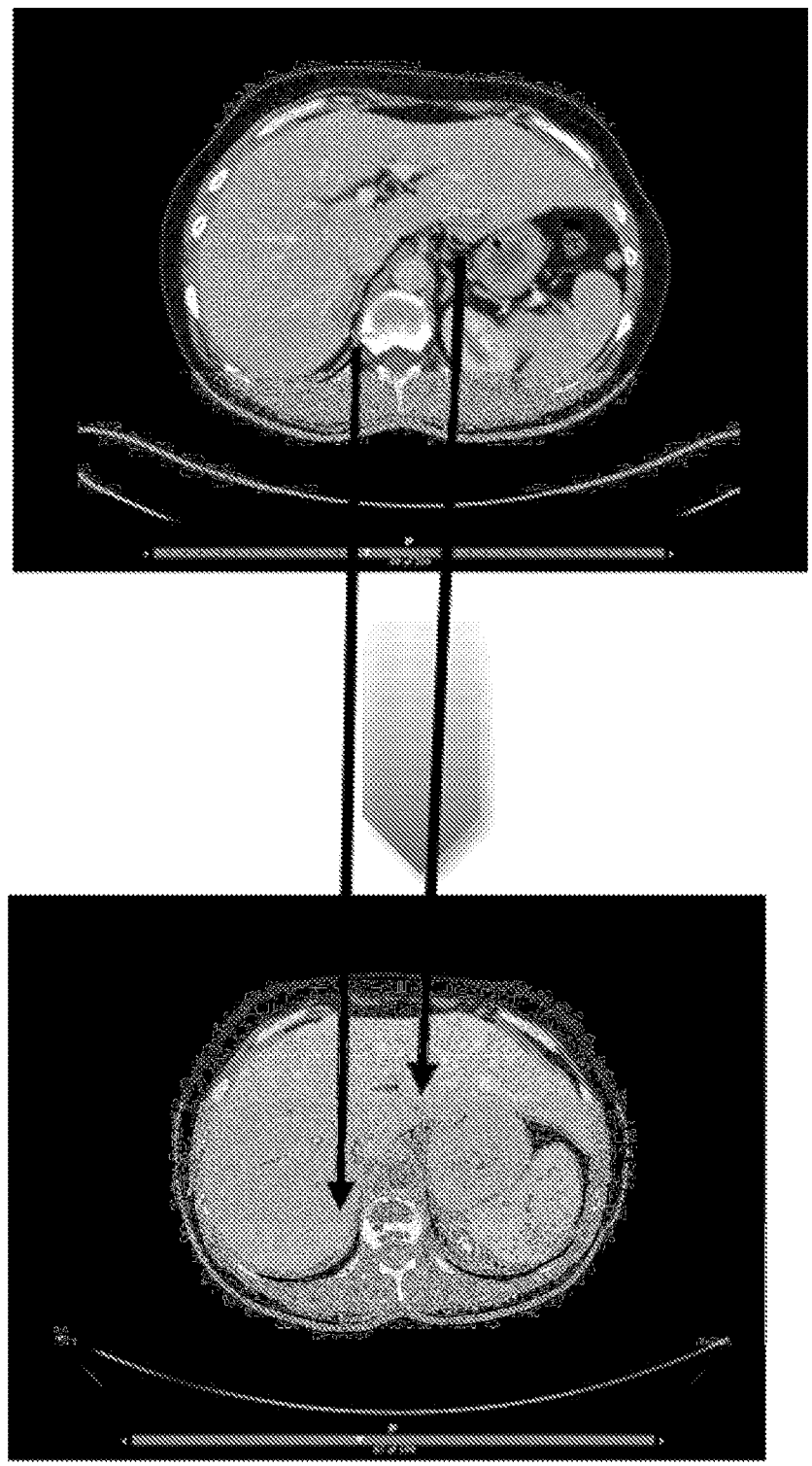

In so far tested, the screening results are in accordance with the individual patient's response to therapy. In FIG. 2c CT scanning of the patient showing moderate sensitivity show correspondence to the screening results (shown in FIG. 2b) in that tumor remission is observed after treatment with compounds predicted to be effective in the screening test.

Figure 3:
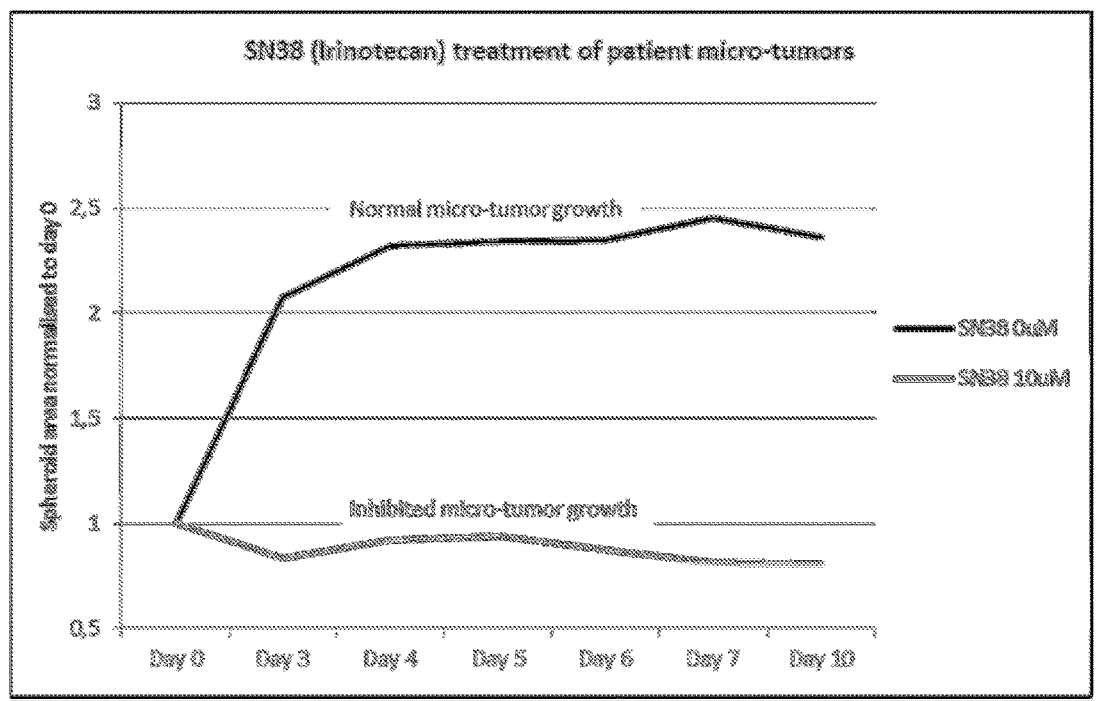
FIG. 3 shows time trace of Micro-tumor growth in the presence and absence of the chemo therapeutic compound Irinotecan

FIG. 3 shows an example of time trace of micro-tumour (spheroid) growth in the presence of absence of Irinotecan. In the example shown, Irinotecan clearly inhibited cancer cell proliferation.

Example 5

Screening of Compounds Distributed in Pluronic®
Materials and Solutions:
Array prepared accordingly to Example 1 using Pluronic® 20% in STEM media instead of Matrigel®
STEM media: DMEM/F12 w. 15% Hepes (Gibco 11330-032), StemPro hESC SFM growth supplement (50×): 1×
BSA 25%, Gibco A10008-01: 1.8%, FGF-basic (10 ug/ml): 8 ng/ml, 2-Mercaptoethanol Gibco 21985 (55 mM): 0.1 mM, Penicillin/streptomycin 200 U/ml/200 ug/ml (=2× usual conc.), Gentamycin Sigma G1272: 1:100 (=2× usual conc.), Amphotericin (fungicide): 1:100 (=1× usual conc.), Hepes 15 mM
Incubator, 37° C. (CO2, 99% humidity for cell culture)
Procedure:
1. Tumor tissue from patient was prepared to form a population of small individual micro-tumors (spheroids)
2. Micro-tumors were suspended in 37° C. pre-warmed STEM media
3. The array (stored in freezer) was incubated at 37° C. for 1 hr. to allow Pluronic® to crosslink and thereby solidify (solid)
4. The micro tumor suspension was added to the reservoir of the array
2. The array was incubated for 7 min. at 37° C. to allow cells to settle into individual wells of the array
5. STEM media was gently removed from reservoir—leaving the micro tumors in the wells
6. The array was moved to refrigerator (5° C.) and left for 30 min to allow Pluronic® to liquefy and the cells to settle at the bottom of the array (fluid)
7. Hereafter the array was incubated at 37° C. for 1 hr. to allow the Pluronic® to solidify and fix the cells in a certain position (solid)
8. The array with micro-tumors positioned at the bottom was imaged at an automated microscope
9. Images were acquired every day for 10 days and micro-tumor growth (and inhibition of growth) was measured by quantifying the area of the micro-tumors.

Example 6

Screening of Compounds Imbedded in Thermo Sensitive Nano-Particles Distributed in Matrigel®
Materials and Solutions:
Array prepared accordingly to Example 2
STEM media: DMEM/F12 w. 15% Hepes (Gibco 11330-032), StemPro hESC SFM growth supplement (50×): 1×
BSA 25%, Gibco A10008-01: 1.8%, FGF-basic (10 ug/ml): 8 ng/ml, 2-Mercaptoethanol Gibco 21985 (55 mM): 0.1 mM, Penicillin/streptomycin 200 U/ml/200 ug/ml (=2× usual conc.), Gentamycin Sigma G1272: 1:100 (=2× usual conc.), Amphotericin (fungicide): 1:100 (=1× usual conc.), Hepes 15 mM
Incubator, 37° C. (CO2, 99% humidity for cell culture)
Heating cabinet (to give 42° C.)
Procedure:
1. Tumor tissue from patient was prepared to form a population of small individual micro-tumors (spheroids)
2. Micro-tumors were suspended in cold STEM media
3. The array was taken directly from freezer and placed on the cooling device (solid)
4. The micro tumor suspension was added to the reservoir of the array
3. The array was left for 7 min. to allow cells to distribute and settle into individual wells of the array
5. STEM media was gently removed from reservoir—leaving the micro tumors in the wells
6. The array was moved to refrigerator (5° C.) and left for 30 min to allow Matrigel® to liquefy and the cells to settle at the bottom of the array (fluid)
7. Hereafter the array was incubated at 37° C. for 1 hr. to allow the Matrigel® to solidify and fix the cells in a certain position (solid)
8. The array was following incubated at 42° C. for 12 min to release compounds from nano-particles
9. The array was incubated for 30 min at 37° C. to equilibrate array content to 37° C.
10. The array with micro-tumors positioned at the bottom was imaged at an automated microscope
11. Images were acquired every day for 10 days and micro-tumor growth (and inhibition of growth) was measured by quantifying the area of the micro-tumors.

Figure 4:
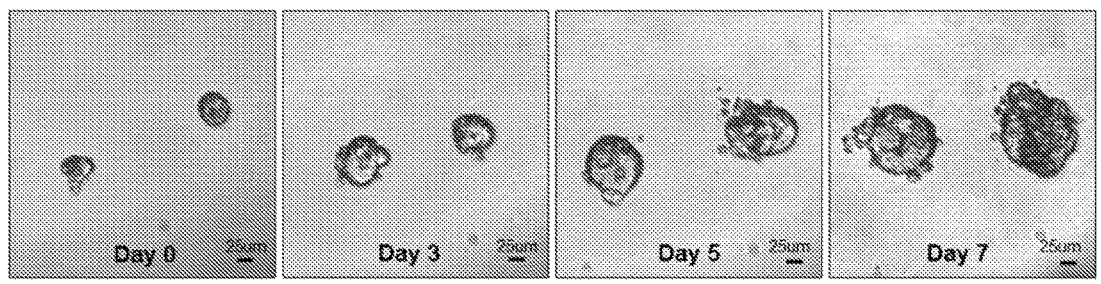
FIG. 4 shows micro-tumor growth under exposure to Irinotecan (SN38) for 10 days in phase shifting support.
Figure 4:
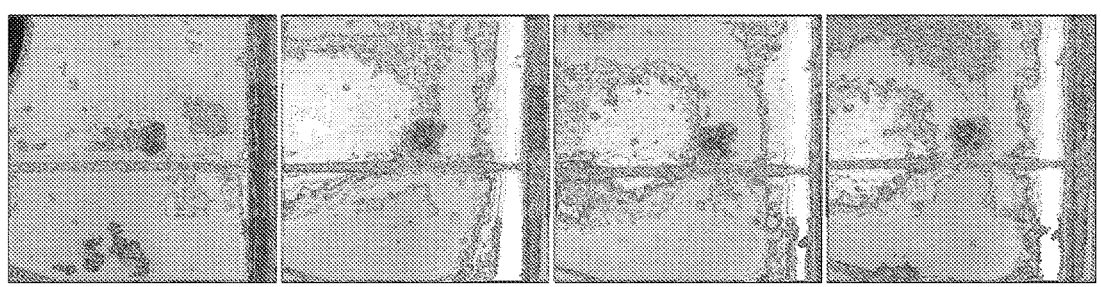

An example of micro-tumour growth is shown in FIG. 4. Images of micro-tumours (spheroids) at day 0, 3, 5 and 7 grown in the absence and presence of Irinotcan were taken under a microscope. As can be seen, Irinotecan inhibits proliferation of these cancer cells.

The invention claimed is:

1. A method of identifying a compound or a combination of compounds that modify a least one cellular phenotype, said method comprising the steps of:
   i) providing a library containing a plurality of library members, herein each library member is a compound or a combinations of compounds;
   ii) providing a suspension of cells which may acquire said cellular phenotype;
   iii) providing a cell-compatible support, wherein the support reversible can change between a sol state and a gel-state;
   iv) providing an array containing a plurality of spaces;
   v) adding said support in sol-state to the spaces of said array;
   vi) adding library members to the spaces of said array, wherein at least two different library members are added to two different spaces,
   wherein steps v) and vi) may be performed simultaneously or sequentially in any order,
   vii) bringing the support to the eel-state;
   viii) contacting the spaces of said array with the suspension of cells; and
   ix) bringing the support into the sol-state,
   wherein steps viii) and ix) may be performed simultaneously or sequentially in any order; and
   x) bringing the support to the gel-state thereby entrapping cells in the support; and
   xi) incubating the array under conditions allowing maintenance and/or growth of the cells,
   xii) detecting the cellular phenotype in the cells,
   xiii) identifying library members modifying the cellular phenotype,
   thereby identifying a compound or a combination of compounds modifying said cellular phenotype.

2. The method according to claim 1, wherein said support is a temperature reversible gel.

3. The method according to claim 1, wherein said support is a sol-gel with a sol-gel transition temperature in the range of 0 to 35° C.

4. The method according to claim 1, wherein the support is a hydrogel selected from the group consisting of gelatinous gels and, copolymers, wherein the copolymer for example may be pluronic lecithin organogels or alginate hydrogels.

5. The method according to claim 1, wherein the array is a container comprising a plurality of compartments, which are separated by physical barriers.

6. The method according to claim 5, wherein steps v) and vi) comprises adding the support and the library members to said compartments or wells, wherein at least two different library members are added to two different compartments or wells.

7. The method according to claim 1, wherein the cells are cells resected from a human being.

8. The method according to claim 7, wherein the cells are cancer cells provided at least in part in the form of spheroids and the cellular phenotype is in vitro growth of said spheroids.

9. The method according to claim 1, wherein the cell are primary cancer cells.

10. The method according to claim 1, wherein the cellular phenotype is selected from the group consisting of cell proliferation and cell death.

11. The method according to claim 1, wherein one or more library me are drugs) useful in cancer treatment or a combination of drugs useful in cancer treatment.

12. The method according to claim 1, wherein the method comprises the steps of:
   i) providing an array comprising a plurality of spaces, wherein each space comprises a cell-compatible support, wherein the support reversible can change between a sol-state and a gel-state; and
   wherein at least 2 spaces further comprises different library members; and
   wherein each library member is a compound or a combination of compounds, and
   wherein the support is in the gel-state
   ii) providing a suspension of cells which may acquire said cellular phenotype;
   iii) contacting the spaces of said array with the suspension of cells; and
   iv) bringing the support into the sol-state
   wherein steps iii) and iv) may be performed simultaneously or sequentially in any order; and
   v) bringing the support to the gel-state thereby entrapping cells in the support; and
   vi) incubating the array under conditions allowing maintenance and/or growth of the cells,
   vii) detecting the cellular phenotype in the cells,
   viii) identifying library members modifying the cellular phenotype,
   thereby identifying a compound or a combination of compounds modifying said cellular phenotype.

13. A method of treatment of a clinical condition characterized by at least one cellular phenotype in an individual in need thereof, said method comprising the steps of:
   i) obtaining cells associated with said clinical condition from an individual suffering from said clinical condition;
   ii) identifying a compound or a combination of compounds modifying said at least one cellular phenotype characterizing said clinical condition by the method according to claim 1,
   iii) administering a therapeutically effective amount of said compound or combination of compounds to said individual,
   thereby treating said clinical condition.

14. The method according to claim 13, wherein the cells are causative of said clinical condition.

15. The method according to claim 13, wherein the clinical condition is cancer.

16. The method according to claim 15, wherein the cellular phenotype is in vitro cancer cell proliferation.

17. The method according to claim 15, wherein one or more library members are drugs useful in cancer treatment or a combination of drugs useful in cancer treatment.

18. The method according to claim 15, wherein the method is a method for predicting the efficacy of treatment of a cancer in an individual in need thereof, the method comprising the steps of:
   i) providing an array comprising a plurality of spaces, wherein each space comprises a cell-compatible support, wherein the support reversible can change between a sol-state and a gel-state; and
   wherein at least 2 spaces further comprises different library members; and wherein each library member is a drug or a combination of drugs useful in the treatment of cancer, and
wherein the support is in the gel-state
ii) providing a suspension of cancer cells or cancer cells in spheroids obtained from said individual;
iii) bringing the support to the gel-state;
iv) contacting the spaces of said array with the suspension of cells; and
v) bringing the support into the sol-state
wherein steps iv) and v) may be performed simultaneously or sequentially in any order;
vi) bringing the support to the gel-state thereby entrapping cells in the support; and
vii) incubating the array under conditions allowing growth of the cells
viii) detecting cancer cell proliferation and/or growth of cancer cell spheroids,
ix) identifying library members inhibiting proliferation of cancer cells and/or growth of cancer cell spheroids
wherein library members inhibiting proliferation of cancer cells and/or growth of cancer cell spheroids are predicted to be effective in treatment of cancer in said individual.

* * * * *